(12) United States Patent
Fuchs et al.

(10) Patent No.: US 8,629,272 B2
(45) Date of Patent: Jan. 14, 2014

(54) TRICYCLIC PYRIMIDINE DERIVATIVES AS WNT ANTAGONISTS

(75) Inventors: Florian Fuchs, Basel (CH); Daniel Gilbert, Nürnberg (DE); Corinna Koch, Einhausen (DE); Rajendra-Prasad Maskey, Heidelberg (DE); Sandra Steinbrink, Mainz (DE); Michael Boutros, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 13/380,459

(22) PCT Filed: Jun. 25, 2010

(86) PCT No.: PCT/EP2010/059097
§ 371 (c)(1),
(2), (4) Date: Mar. 8, 2012

(87) PCT Pub. No.: WO2010/149783
PCT Pub. Date: Dec. 29, 2010

(65) Prior Publication Data
US 2012/0157481 A1     Jun. 21, 2012

(30) Foreign Application Priority Data
Jun. 26, 2009 (EP) .................................... 09163929

(51) Int. Cl.
*C07D 491/00* (2006.01)
*A61K 31/505* (2006.01)

(52) U.S. Cl.
USPC ......................................... 544/251; 514/267

(58) Field of Classification Search
USPC ..................... 514/267; 435/375; 544/251
See application file for complete search history.

(56) References Cited

U.S. PATENT DOCUMENTS

| 5,041,138 A | 8/1991 | Vacanti et al. |
| 2007/0219257 A1 | 9/2007 | Beachy et al. |

FOREIGN PATENT DOCUMENTS

| JP | 52-085194 | | 7/1977 |
| JP | 52085194 A | * | 7/1977 |
| WO | WO 03/045951 A1 | | 6/2003 |
| WO | WO 2006/135627 A2 | | 12/2006 |
| WO | WO 2006135627 A2 | * | 12/2006 |

OTHER PUBLICATIONS

National Institutes of Health (NIH). "Dementia." Available at: < http://www.nlm.nih.gov/medlineplus/ency/article/000739.htm>.*
Seniorjournal.com. "Science Finding Alzheimer's Hard to Treat; Best Strategy May Be Prevention." Available at: < http://seniorjournal.com/News/Alzheimers/2010/20100614-ScienceFindingAlzheimers.htm>.*
Garber, Ken. "Drugging the Wnt Pathway: Problems and Progress." JNCI. (Apr. 15, 2009), vol. 101, Issue 8, pp. 548-550.*
National Institutes of Health (NIH). "Dementia." Available at: < http://www.nlm.nih.gov/medlineplus/ency/article/000739.htm>. Last Updated: Sep. 26, 2011.*
International Search Report cited in related International Patent Application No. PCT/EP2010/059097, completed Sep. 13, 2010.
Barker et al., "Mining the Wnt Pathway for Cancer Therapeutics," *Nature Reviews*, vol. 5, pp. 997-1014 (2006).
Nusse, "Wnt Signaling in Disease and in Development," *Cell Research*, vol. 15, pp. 28-32 (2005).
Huang et al., "Tankyrase Inhibition Stabilizes Axin and Antagonizes Wnt Signalling," *Nature*, vol. 561, pp. 614-620 (2009).
Lu et al., "Spiperone Enhances Intracellular Calcium Level and Inhibits the Wnt Signaling Pathway," *BMC Pharm.*, vol. 9, No. 13, pp. 1-8 (2009).
Li et al., Calpain as an Effector of the Gq Signaling Pathway for Inhibition of Wnt/β-catenin-regulated Cell Proliferation, *PNAS*, vol. 99, pp. 13254-13259 (2002).
Apelqvist et al., "Sonic Hedgehog Directs Specialised Mesoderm Differentiation in the Intestine and Pancreas," *Curr. Biol*, vol. 7, pp. 801-804 (1997).
Bellusci et al., "Involvement of Sonic Hedgehog (Shh) in Mouse Embryonic Lung Growth and Morphogenesis," *Development*, vol. 124, pp. 53-63 (1997).
Fujita et al., "Involvement of Sonic Hedgehog in the Cell Growth of LK-2 Cells, Human Lung Squamous Carcinoma Cells," *Biochemical, and Biophysical Research Communications*, vol. 238, pp. 658-664 (1997).
Stone et al., "Future Directions, Collagen-Based Prostheses for Meniscal Regeneration," *Clin. Orthop. Relat. Red.*, vol. 252, pp. 129-135 (1990).
Grande et al., "The Repair of Experimentally Produced Defects in Rabbit Articular Cartilage by Autologous Chondrocyte Transplantation," *Journ. Of Orthopaedic Res.*, vol. 7, pp. 208-218 (1989).
Takigawa et al., "Chondrocytes Dedifferentiated by Serial Monolayer Culture Form Cartilage Nodules in Nude Mice," *Bone and Mineral*, vol. 2, pp. 449-462 (1987).

(Continued)

*Primary Examiner* — Noble Jarrell
*Assistant Examiner* — John S Kenyon
(74) *Attorney, Agent, or Firm* — Foley & Lardner LLP

(57) ABSTRACT

The present invention relates to compounds having the general formula (I) with the definitions of X1-X3, Y1, Y2, L1, R1 and R2 given below and/or solvates, hydrates, esters and pharmaceutically acceptable salts thereof. Furthermore, the invention relates to the use of said compounds for modulating of the Wnt signalling pathway activity and their use as a medicament, preferably for the treatment of cancer.

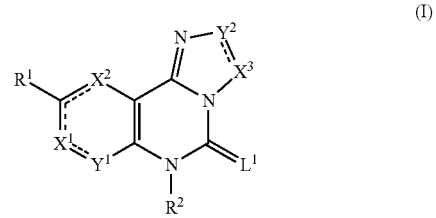

19 Claims, No Drawings

(56) References Cited

OTHER PUBLICATIONS

Wakitani et al., "Repair of Rabbit Articular Surfaces with Allograft Chondrocytes Embedded in Collagen Gel.," *J. Bone Jt. Surg.*, vol. 71, pp. 74-80 (1989).

Vacanti et al., "Synthetic Polymers Seeded with Chondrocytes Provide a Template for New Cartilage Formulation," *Plastic Reconstr. Surg.*, vol. 88, pp. 753-759 (1991).

Von Schroeder et al., "The use of Polylactic.Acid Matrix and Periosteal Grafts for the Reconstruction of Rabbit Knee Articular Defects," *J. Biomed. Mater. Res.*, vol. 25, pp. 329-339 (1991).

Freed et al., "Neocartilage Formation in vitro and in vivo using Cells Cultured on Synthetic Biodegradable Polymers," *Journ. Of Biomedical Materials Research*, vol. 27, pp. 11-23 (1993).

Goodrich et al., "Altered Neural Cell Fates and Medulloblastoma in Mouse Patched Mutants," vol. 277, pp. 1109-1113 (1997).

Xie et al., "Mutations of the Patched Gene in Several Types of Sporadic Extracutaneous Tumors," *Cancer Res.*, vol. 57, pp. 2369-2372 (1997).

Oro et al., "Basal Cell Carcinomas in Mice Overexpressing Sonic Hedgehog," *Science*, vol. 276, pp. 817-821 (1997).

Xie et al., "Physical Mapping of the 5 Mb D9S196-D9S180 Interval Harboring the Basal Cell Nevus Syndrome Gene and Localization of Six Genes in This Region," *Genes Chromosomes Cancer*, vol. 18, pp. 305-309 (1997).

Stone et al., "The Tumour-Suppressor Gene Patched Encodes a Candidate Receptor for Sonic Hedgehog," *Nature*, vol. 384, pp. 129-134 (1996).

Johnson et al., "Human Homolog of Patched, a Candidate Gene for the Basal Cell Nevus Syndrome," *Science*, vol. 272, pp. 1668-1671 (1996).

Sefton et al., "Implantable Pumps," *Crit. Ef. Biomed. Eng.*, vol. 14, pp. 201-240 (1987).

Buchwald et al., "Long-term, Continuous Intravenous Heparin Administration by an Implantable Infusion Pump in Ambulatory Patients with Recurrent Venous Thrombosis," *Surgery*, vol. 88, pp. 507-516 (1980).

Saudek et al., "Preliminary Trial of the Programmable Implantable Medication System for Insulin Delivery," *The New Engl. Journ. Of Med.*, vol. 321, pp. 574-579 (1989).

Langer et al., "Chemical and Physical Structure of Polymers as Carriers for Controlled Release of Bioactive Agents: A Review," *Macromol. Sci. Rev. Macromol. Chem..*, vol. 23, pp. 61-126 (1983).

Levy et al., "Inhibition of Calcification of Bioprosthetic Heart Valves by Local Controlled-Release Diphosphonate," *Science*, vol. 228, pp. 190-192 (1985).

During et al., "Controlled Release of Dopamine from a Polymeric Brain Implant: In Vivo Characterization," *Ann. Neurol.*, vol. 25, pp. 351-356 (1989).

Howard et al., "Acute Subdural Hematomas: An Age-Dependent Clinical Entity," *J. Neurosurg*, vol. 71, pp. 858-863 (1989).

Goodson, "Medical Applications of Controlled Release," vol. 2, pp. 115-138 (1984).

Langer, "New Method of Drug Delivery," *Science*, vol. 249, pp. 1527-1533 (1990).

Van de Wetering, et al., "Armadillo Coactivates Transcription Driven by the Product of the Drosophila Segment Polarity Gene dTCF," *Cell*, vol. 88, pp. 789-799 (1997).

Davidson et al., "Casein Kinase 1 gamma Couples Wnt Receptor Activation to Cytoplasmic Signal Transduction," *Nature*, vol. 438, pp. 867-872 (2005).

\* cited by examiner

TRICYCLIC PYRIMIDINE DERIVATIVES AS WNT ANTAGONISTS

The present invention relates to compounds having the general formula (I) with the definitions of X1-X3, Y1, Y2, L1, R1 and R2 given below and/or solvates, hydrates, esters and pharmaceutically acceptable salts thereof. Furthermore, the invention relates to the use of said compounds for modulating of the Wnt signalling pathway activity and their use as a medicament, preferably for the treatment of cancer.

The Wnt signalling pathway plays an important role in the regulation of cell proliferation and differentiation. Aberrant activation of the Wnt signalling pathway is known to promote uncontrolled cell growth and survival and can therefore be a major driving force in a broad spectrum of human cancers and diseases. For example, the inhibition of aberrant Wnt signalling pathway activity in cancer cell lines effectively blocks their growth (N. Barker and H. Clevers "Mining the Wnt pathway for cancer therapeutics", Nature Reviews, vol. 5, 2007, pages 997-1014; R. Nusse, "Wnt signalling in disease and in development", Cell Research, Vol. 15, 2005, pages 23-32). Other disorders and diseases are considered to be influenced by an aberrant Wnt signalling pathway, too (see literature cited above).

The Wnt signalling pathway involves a large number of proteins regulating the production of Wnt signalling molecules, their interaction with receptors on target cells and the physiological response of target cells resulting from the exposure of cells to the extra-cellular Wnt ligands.

Secreted signalling proteins of the Wnt family bind to specific Frizzled (Frz) receptor complexes on the surface of target cells and activate distinct intracellular pathways that are broadly classified as canonical or non-canonical Wnt signalling pathways.

In brief, the canonical pathway regulates the amount of the protein beta-catenin in a cell and its ability to enter the nucleus of the cell, where it interacts with members of the Tcf/Lef protein family. Beta-catenin and Tcf form active transcription factor complexes in the nucleus and activate the Wnt target gene. The presence of the Tcf-beta-catenin complex in the nucleus is a hallmark in the Wnt signalling pathway indicating its activation. An overview of the Wnt signalling pathway can be found in N. Barker and H. Clevers "Mining the Wnt pathway for cancer therapeutics", Nature Reviews, vol. 5, 2007, pages 997-1014.

The constant presence of Tcf-beta-catenin complexes in the nuclei of cells leads to chronic activation of the genetic program considered to promote cancer formation by stimulating cell growth, blocking apoptosis and altering cell movement. For instance, the artificial disruption of Tcf-beta-catenin complex formation in colon cancer cells effectively blocks target gene activation and inhibits the growth in vitro. Drugs designed to inhibit the Wnt signalling pathway and consequently the formation of the Tcf-beta-catenin complex in the nucleus of a cell are therefore expected to hold great potential for the treatment of a range of cancers and other diseases associated with the Wnt signalling pathway.

Therefore, there is a strong need for novel compounds which modulate the Wnt signalling pathway thereby opening new routes for the treatment of disorders and/or diseases associated with an aberrant activation of Wnt signalling.

An object of the present invention is to provide such compounds. This object is achieved by a compound having the general formula (I)

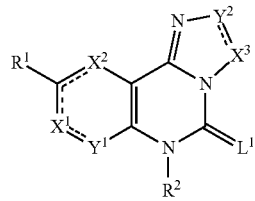

X1: CR3R4 or CR3;
X2: C=L2, CR5R6 or CR5;
X3: CR7R8 or CR7;
Y1: NR9 or N;
Y2: NR10 or N;
wherein
the dotted lines denote 1 to 3 optional double bonds between Y1 and X1,
X1 and C(R1), C(R1) and X2 or between Y and X1 and simultaneously between C(R10) and X2 and/or between Y2 and X3;
L1 and L2 are independently from each other selected from the group comprising NR11, O and S;
R1 is selected from the group comprising H, OH, OR15, COOH, COOR15, CHO, CONR15R16, C=N—OR15, C=N—NR15R16, C=N—NR15-COR16, $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl wherein the alkyl, alkoxy, acyl, alkenyl, alkinyl, cycloalkyl, cycloalkenyl, aryl, aryloxy and aralkyl may contain 1 to 4 heteroatoms selected from N, O and S and/or functional groups selected from CO in the chain or cycle and may be substituted by one or more substituents selected independently from each other from the group comprising $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy, $C_4$-$C_{15}$ aralkyl, F, Cl, Br, I, CN, CHO, OH, OR12, SR12, NR12R13, COOH, COOR12, CONR12R13, $SO_2$R12, $SO_2$NR12R13, SONR12R13, NR12SOR13, NR12$SO_2$R13, NR12$SO_2$NR13R14, NR12COR13, NR12CONR13R14, NR12COOR13, OCONR12R13 wherein the alkyl, alkoxy, acyl, alkenyl, alkinyl, cycloalkyl, cycloalkenyl, aryl, aryloxy and aralkyl may contain 1 to 4 heteroatoms selected from N, O and S and/or functional groups selected from CO in the chain or cycle;
or R1 forms together with R3 a 5 to 7 membered saturated or unsaturated ring having a lactam, lacton, diimid or anhydride or 1 to 2 ether bondings, wherein the 5 to 7 membered ring may be substituted by one or more substitutents selected independently from each other from the group comprising F, Cl, Br, I, CN, CHO, OH, OR12, SR12, NR12R13, COOH, COOR12, CONR12R13, $SO_2$R12, $SO_2$NR12R13, SONR12R13, NR12SOR13, NR12$SO_2$R13, NR12$SO_2$NR13R14, NR12COR13, NR12CONR13R14, NR12COOR13, OCONR12R13, $C_1$-$C_8$ alkyl, $C_1$-$C_8$ alkoxy, $C_1$-$C_8$ acyl, $C_2$-$C_8$ alkenyl, $C_3$-$C_8$ cycloalkyl, $C_3$-$C_8$ cycloalkenyl, $C_3$-$C_7$ aryl, $C_4$-$C_{13}$ aralkyl and $C_3$-$C_7$ aryloxy wherein the alkyl, alkoxy, acyl, alkenyl, alkinyl, cycloalkyl, cycloalkenyl, aryl, aralkyl and aryloxy may contain 1 to 4 heteroatoms selected from N, O and S and/or functional groups selected from CO in the chain or cycle and may be substituted by one or more substituents selected independently from each other from the group comprising $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy, $C_4$-$C_{15}$ aralkyl, F, Cl, Br, I, CN, CHO, OH, OR12, SR12, NR12R13, COOH, COOR12, CONR12R13, SO$_2$R12, SO$_2$NR12R13, SONR12R13, NR12SOR13, NR12SO$_2$R13, NR12SO$_2$NR13R14, NR12COR13, NR12CONR13R14, NR12COOR13, OCONR12R13 wherein the alkyl, alkenyl, alkoxy, acyl, alkenyl, alkinyl, cycloalkyl, cycloalkenyl, aryl, aryloxy and aralkyl may contain 1 to 4 heteroatoms selected from N, O and S and/or functional groups selected from CO in the chain or cycle;

R2 is selected from the group comprising H, $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl wherein the alkyl, alkoxy, acyl, alkenyl, alkinyl, cycloalkyl, cycloalkenyl, aryl, aryloxy and aralkyl may contain 1 to 4 heteroatoms selected from N, O and S and/or functional groups selected from CO in the chain or cycle and may be substituted by one or more substituents selected independently from each other from the group comprising $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy, $C_4$-$C_{15}$ aralkyl, F, Cl, Br, I, CN, CHO, OH, OR12, SR12, NR12R13, COOH, COOR12, CONR12R13, SO$_2$R12, SO$_2$NR12R13, SONR12R13, NR12SOR13, NR12SO$_2$R13, NR12SO$_2$NR13R14, NR12COR13, NR12CONR13R14, NR12COOR13, OCONR12R13 wherein the alkyl, alkoxy, acyl, alkenyl, alkinyl, cycloalkyl, cycloalkenyl, aryl, aryloxy and aralkyl may contain 1 to 4 heteroatoms selected from N, O and S and/or functional groups selected from CO in the chain or cycle;

R3 and R4 are selected independently from each other from the group comprising H, $C_1$-$C_8$ alkyl, $C_2$-$C_6$ alkenyl, $C_3$-$C_7$ cycloalkyl and $C_3$-$C_7$ aryl, wherein the alkyl, alkenyl, cyloalkyl and aryl may contain 1 to 4 hetero atoms selected from the group comprising N, O and S and/or functional groups selected from CO and may be substituted by one or more substituents selected from F, Cl, Br, I, CN, CHO, OH, OR12, SR12, NR12R13, COOH, COOR12, CONR12R13, SO$_2$R12, SO$_2$NR12R13, SONR12R13, NR12SOR13, NR12SO$_2$R13, NR12SO$_2$NR13R14, NR12COR13, NR12CONR13R14, NR12COOR13, OCONR12R13;

or R3 forms together with R1 a 5 to 7 membered saturated or unsaturated ring having a lactam, lacton, diimid or anhydride or 1 to 2 ether bondings, wherein the 5 to 7 membered ring may be substituted by one or more substitutents selected independently from each other from the group comprising F, Cl, Br, I, CN, CHO, OH, OR12, SR12, NR12R13, COOH, COOR12, CONR12R13, SO$_2$R12, SO$_2$NR12R13, SONR12R13, NR12SOR13, NR12SO$_2$R13, NR12SO$_2$NR13R14, NR12COR13, NR12CONR13R14, NR12COOR13, OCONR12R13, $C_1$-$C_8$ alkyl, $C_1$-$C_8$ alkoxy, $C_1$-$C_8$ acyl, $C_2$-$C_8$ alkenyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl wherein the alkyl, alkoxy, acyl, alkenyl, cycloalkyl, cycloalkenyl, aryl, aryloxy and aralkyl may contain 1 to 4 heteroatoms selected from N, O and S and/or functional groups selected from CO in the chain or cycle and may be substituted by one or more substituents selected independently from each other from the group comprising $C_1$-$C_8$ alkyl, $C_1$-$C_8$ alkoxy, $C_1$-$C_8$ acyl, $C_2$-$C_8$ alkenyl, $C_3$-$C_8$ cycloalkyl, $C_3$-$C_8$ cycloalkenyl, $C_3$-$C_7$ aryl, $C_3$-$C_7$ aryloxy, F, Cl, Br, I, CN, CHO, OH, OR12, SR12, NR12R13, COOH, COOR12, CONR12R13, SO$_2$R12, SO$_2$NR12R13, SONR12R13, NR12SOR13, NR12SO$_2$R13, NR12SO$_2$NR13R14, NR12COR13, NR12CONR13R14, NR12COOR13, OCONR12R13 wherein the alkyl, alkoxy, acyl, alkenyl, cycloalkyl, cycloalkenyl, aryl and aryloxy may contain 1 to 4 heteroatoms selected from N, O and S and/or functional groups selected from CO in the chain or cycle;

R5 and R6 are selected independently from each other from the group as defined for R3 and R4 with the proviso that neither R5 nor R6 form a 5- to 7-membered ring with R1;

R7 and R8 are independently from each other selected from the group comprising H, $C_1$-$C_8$ alkyl, $C_2$-$C_8$ alkenyl, $C_3$-$C_8$ cycloalkyl, $C_3$-$C_8$ cycloalkenyl and $C_3$-$C_7$ aryl, $C_3$-$C_7$ aryloxy and $C_4$-$C_{15}$ aralkyl wherein the alkyl, alkenyl, cycloalkyl, cycloalkenyl, aryl, aryloxy and aralkyl may contain 1 to 4 heteroatoms selected from N, O and S and/or functional groups selected from CO in the chain or cycle and may be substituted by one or more substituents selected independently from each other from the group comprising $C_1$-$C_8$ alkyl, $C_1$-$C_8$ alkoxy, $C_1$-$C_8$ acyl, $C_2$-$C_8$ alkenyl, $C_3$-$C_8$ cycloalkyl, $C_3$-$C_8$ cycloalkenyl, $C_3$-$C_7$ ary,l, $C_3$-$C_7$ aryloxy, $C_4$-$C_{15}$ aralkyl, F, Cl, Br, I, CN, CHO, OH, OR12, SR12, NR12R13, COOH, COOR12, CONR12R13, SO$_2$R12, SO$_2$NR12R13, SONR12R13, NR12SOR13, NR12SO$_2$R13, NR12SO$_2$NR13R14, NR12COR13, NR12CONR13R14, NR12COOR13, OCONR12R13 wherein the substituents alkyl, alkoxy, acyl, alkenyl, alkinyl, cycloalkyl, cycloalkenyl, aryl, aryloxy and aralkyl optionally contain 1 to 4 heteroatoms selected from N, O and S and/or functional groups selected from CO in the chain or cycle, wherein the alkyl, alkoxy, acyl, alkenyl, cycloalkyl, cycloalkenyl, aryl, aryloxy and aralkyl may be substituted by one or more substituents selected from the group OH, F, Cl, Br, I, CN, NH$_2$, $C_1$-$C_4$ alkyl, $C_2$-$C_4$ alkenyl, $C_1$-$C_4$ alkoxy, $C_5$-$C_7$ aryl, $C_3$-$C_8$ cycloalkyl and $C_5$-$C_7$ aryloxy;

R9 and R10 are selected independently from each other from the group as defined for R2;

R11 is selected from the group comprising H, $C_1$ to $C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl, optionally containing 1 to 4 heteroatoms selected from N, O and S;

R12, R13, R14, R15 and R16 are selected independently from each other from the group H, OH, $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl, optionally containing 1 to 4 heteroatoms selected from N, O and S and/or functional groups selected from CO in the chain or cycle, wherein the alkyl, alkoxy, acyl, alkenyl, alkinyl, cycloalkyl, cycloalkenyl, aryl, araloxy and aralkyl may be substituted by one or more substituents selected from the group OH, F, Cl, Br, I, CN, $C_1$-$C_4$ alkyl, $C_2$-$C_4$ alkenyl, $C_1$-$C_4$ alkoxy, $C_5$-$C_7$ aryl, $C_3$-$C_8$ cycloalkyl and $C_5$-$C_7$ aryloxy;

wherein alkyl, alkenyl, alkoxy, acyl, alkenyl, alkinyl and aralkyl may be present linear or branched;

and/or solvates, hydrates, esters, and pharmaceutically acceptable salts thereof.

"Alkyl" means a linear or branched saturated aliphatic hydrocarbon group.

"Alkenyl" means a linear or branched unsaturated aliphatic hydrocarbon group with at least one double bond.

"Alkinyl" means a linear or branched unsaturated aliphatic hydrocarbon group with at least one triple bond.

"Alkoxy" means the group O-alkyl, wherein "alkyl" is defined as above.

"Acyl" means $(CO)H(C_1$ acyl) and CO-alkyl ($C_2$-$C_8$ acyl), wherein "alkyl" is defined as above.

"Cycloalkyl" means a saturated 3 to 8-member hydrocarbon ring.

"Cycloalkenyl" means a partially unsaturated 3- to 8-membered hydrocarbon ring having at least one double bond in the cycle.

"Aryl" means an aromatic 3- to 7-numbered hydrocarbon ring.

"Aryloxy" denotes an O— aryl-group wherein "aryl" is defined as above.

"Aralkyl" means a $C_3$-$C_7$ aryl group substituted with at least one $C_1$-$C_8$ alkyl group, wherein aryl and alkyl are defined as above.

The above defined groups alkyl, alkoxy, acyl, alkenyl, alkinyl, cycloalkyl, cycloalkenyl, aryl, aralkyl and aryloxy may contain 1 to 4 heteroatoms selected from the group N, O and S and/or functional groups from CO in the chain or cycle. The heteroatoms optionally present in the chain or the cycle of a substituent replace a =CH$_2$—, a —CH=, a —C≡, or a =C= group in the chain or cycle, the CO-group replaces a CH$_2$-group in the chain or cycle. Preferably, the heteroatoms are present in the chain or cycle of a substituent as —O—, —S—, —SO—, —SO$_2$—, —NR'— and —N=, wherein R' is H or the residual part of the substituent. The numbers 1 to 4 relate to the total number of heteroatoms plus CO-groups present in the respective substituent.

Preferred $C_3$-$C_8$ cycloalkyl groups containing 1 to 4 heteroatoms selected from the group N, O and S are derived from the following heterocyclic compounds: tetrahydrofurane, pyrrolidine, tetrahydrothiophene, oxazolidine, piperidine, tetrahydropyrane, piperazine, dioxane, morpholine and trioxane.

Preferred $C_3$-$C_7$ aryl groups containing 1 to 4 heteroatoms selected from the group N, O and S are derived from the following heteroaromatic compounds: Pyrrole, pyrazole, imidazole, triazole, tetrazole, furane, thiophene, oxazole, isoxazole, thiazole, isothiazole, thiadiazole, pyridine, pyridazine, pyrimidine, pyrazine and triazine and tetrazine.

For C-atoms being part of the tricyclus at the positions of Y1, X1, C(R1), X2, Y2 and X3 it is possible to form a double bond with an adjoined C-atom. According to the invention double bonds are optionally present between Y1 and X1, between X1 and C(R1), between C(R1) and X2 and/or between Y2 and X3. There are several combinations of double bonds possible in the tricyclus, namely a double bond between Y2 and X3 alone or in combination with double bonds between Y1 and X1, between X1 and C(R1), between C(R1) and X2, or between Y1 and X1 and simultaneously between C(R1) and X2. The tricyclus of formula I therefore may contain 1 to 3 double bonds. For X1, X2 and X3 it depends on the presence or absence of a double bond in the tricyclus whether X1, X2, and/or X3 represent a C-atom with one substituent (in the presence of a double bond which includes the respective C-atom) or a C-atom with two substituents (in the absence of a double bond which includes the respective C-atom), respectively. If a C-atom takes part in a double bond, it is represented by CR, if it does not, it is denoted by CRR'. The same applies to Y1 and Y2 analogously.

According to a preferred embodiment of the invention at least on of the substituents R1, R3 or R5 is not H.

According to another preferred embodiment of the invention X1-X3, Y1, Y2, L1, R1 and R2 of formula (I) are defined as above with the proviso that if Y2 is NR10 then R10 is selected from the group comprising $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl wherein the alkoxy, acyl, alkenyl, alkinyl, cycloalkyl, cycloalkenyl, aryl, aryloxy and aralkyl may contain 1 to 4 heteroatoms selected from N, O and S and/or functional groups selected from CO in the chain or cycle and may be substituted by one or more substituents selected independently from each other from the group comprising $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy, $C_4$-$C_{15}$ aralkyl, F, Cl, Br, I, CN, CHO, OH, OR12, SR12, NR12R13, COOH, COOR12, CONR12R13, SO$_2$R12, SO$_2$NR12R13, SONR12R13, NR12SOR13, NR12SO$_2$R13, NR12SO$_2$NR13R14, NR12COR13, NR12CONR13R14, NR12COOR13, OCONR12R13 wherein the alkyl, alkoxy, acyl, alkenyl, alkinyl, cycloalkyl, cycloalkenyl, aryl, aryloxy and aralkyl may contain 1 to 4 heteroatoms selected from N, O and S and/or functional groups selected from CO in the chain or cycle;

In a preferred embodiment of the invention the substituents X1-X3, Y1, Y2, L1, R1 and R2 of formula (I) are defined as following:

X1: CR3R4 or CR3;
X2: C=L2, CR5R6 or CR5;
X3: CR7R8 or CR7;
Y1: NR9 or N;
Y2: NR10 or N;
wherein
the dotted lines denote 1 to 3 optional double bonds between
X1 and C(R1), C(R1) and X2 or between Y1 and X1 and simultaneously between C(R1) and X2 and/or between Y2 and X3;
L1 and L2 are O;
R1 is selected from the group comprising H, OH, OR15, COOH, COOR15, CHO, CONR15R16, C=N—OR15, C=N—NR15-COR16, $C_1$-$C_8$ alkyl, $C_2$-$C_8$ alkenyl, $C_3$-$C_8$ cycloalkyl, $C_3$-$C_7$ aryl and $C_4$-$C_{15}$ aralkyl wherein the alkyl, alkenyl, cycloalkyl, aryl and aralkyl may contain 1 to 4 heteroatoms selected from N, O and S in the chain or cycle and may be substituted by one or more substituents selected independently from each other from the group comprising $C_1$-$C_8$ alkyl, $C_1$-$C_8$ alkoxy, $C_3$-$C_7$ aryl, $C_3$-$C_7$ aryloxy, $C_4$-$C_{15}$ aralkyl, F, Cl, Br, I, CN, OH, OR12, SR12, NR12R13, COOH, COOR12, CONR12R13, SO$_2$R12 and SO$_2$NR12R13, wherein the alkyl, alkoxy, aryl, aryloxy and aralkyl may contain 1 to 4 heteroatoms selected from N, O and S in the chain or cycle;

or R1 forms together with R3 a 5 to 7 membered saturated or unsaturated ring having a lactam, lacton, diimid or anhydride bonding, wherein the 5 to 7 membered ring may be substituted by one or more substitutents selected independently from each other from the group comprising F, Cl, Br, I, CN, OH, OR12, SR12, NR12R13, COOH, COOR12, CONR12R13, SO$_2$R12, SO$_2$NR12R13, C$_1$-C$_8$ alkyl, C$_2$-C$_8$ alkenyl, C$_3$-C$_8$ cycloalkyl, C$_3$-C$_7$ aryl and C$_4$-C$_{15}$ aralkyl wherein the alkyl, alkenyl, cycloalkyl, aryl and aralkyl and may contain 1 to 4 heteroatoms selected from N, O and S in the chain or cycle and may be substituted by one or more substituents selected independently from each other from the group comprising F, Cl, Br, I, CN, OH, OR12, SR12, NR12R13, COOH, COOR12, CONR12R13, SO$_2$R12 and SO$_2$NR12R13;

R2 is selected from the group comprising H, C$_1$-C$_8$ alkyl, C$_2$-C$_8$ alkenyl, C$_3$-C$_8$ cycloalkyl, C$_3$-C$_7$ aryl and C$_4$-C$_{15}$ aralkyl wherein the alkyl, alkenyl, cycloalkyl, aryl and aralkyl may contain 1 to 4 heteroatoms selected from N, O and S in the chain or cycle and may be substituted by one or more substituents selected independently from each other from the group comprising C$_1$-C$_8$ alkyl, C$_1$-C$_8$ alkoxy, C$_3$-C$_8$ cycloalkyl, C$_3$-C$_7$ aryl, C$_3$-C$_7$ aryloxy, C$_4$-C$_{15}$ aralkyl, F, Cl, Br, I, CN, OH, OR12, SR12, NR12R13, COOH, COOR12, CONR12R13, SO$_2$R12 and SO$_2$NR12R13, wherein the alkyl, alkoxy, cycloalkyl, aryl, aryloxy and aralkyl may contain 1 to 4 heteroatoms selected from N, O and S in the chain or cycle;

R3 and R4 are selected independently from each other from the group comprising H, C$_1$-C$_8$ alkyl, C$_2$-C$_8$ alkenyl, C$_3$-C$_7$ cycloalkyl and C$_3$-C$_7$ aryl, wherein the alkyl, alkenyl, cyloalkyl and aryl may contain 1 to 4 hetero atoms selected from the group comprising N, O and S and may be substituted by one or more substituents selected from F, Cl, Br, I, CN, OH, OR12, SR12, NR12R13, COOH, COOR12, CONR12R13, SO$_2$R12 and SO$_2$NR12R13, or R3 forms together with R1 a 5 to 7 membered saturated or unsaturated ring having a lactam, lacton, diimid or anhydride bonding, wherein the 5 to 7 membered ring may be substituted by one or more substituents selected independently from each other from the group comprising F, Cl, Br, I, CN, OH, OR12, SR12, NR12R13, COOH, COOR12, CONR12R13, SO$_2$R12, SO$_2$NR12R13, C$_1$-C$_8$ alkyl, C$_2$-C$_8$ alkenyl, C$_3$-C$_8$ cycloalkyl and C$_3$-C$_7$ aryl, wherein the alkyl, alkenyl, cycloalkyl and aryl may contain 1 to 4 heteroatoms selected from N and O in the chain or cycle and may be substituted by one or more substituents selected independently from each other from the group comprising F, Cl, Br, I, CN, OH, OR12, SR12, NR12R13, COOH, COOR12, CONR12R13, SO$_2$R12 and SO$_2$NR12R13;

R5 and R6 are selected independently from each other from the group as defined for R3 and R4 with the proviso that neither R5 nor R6 form a 5- to 7-membered ring with R1;

R7 and R8 are independently from each other selected from the group comprising H, C$_1$-C$_8$ alkyl, C$_2$-C$_8$ alkenyl, C$_3$-C$_8$ cycloalkyl, C$_3$-C$_7$ aryl and C$_4$-C$_{15}$ aralkyl wherein the alkyl, alkenyl, cycloalkyl, aryl and aralkyl may contain 1 to 4 heteroatoms selected from N, O or S in the chain or cycle and may be substituted by one or more substituents selected independently from each other from the group comprising C$_1$-C$_8$ alkyl, C$_1$-C$_8$ alkoxy, C$_2$-C$_8$ alkenyl, C$_3$-C$_7$ aryl, C$_3$-C$_7$ aryloxy, F, Cl, Br, I, CN, OH, OR12, SR12, NR12R13, COOH, COOR12, CONR12R13, SO$_2$R12 and SO$_2$NR12R13 wherein the substituents alkyl, alkoxy, alkenyl, aryl and aryloxy optionally contain 1 to 4 heteroatoms selected from N, O and S in the chain or cycle, wherein the alkyl, alkoxy, alkenyl, aryl and aryloxy may be substituted by one or more substituents selected from the group OH, F, Cl, Br, I, NH$_2$, C$_1$-C$_4$ alkyl, R9 and R10 are selected independently from each other from the group as defined for R2;

R11 is selected from the group comprising H, OH, C$_1$ to C$_8$ alkyl, C$_3$-C$_8$ cycloalkyl, C$_3$-C$_7$ aryl and C$_4$-C$_{15}$ aralkyl, optionally containing 1 to 4 heteroatoms selected from N, O and S;

R12, R13, R14, R15 and R$^{16}$ are selected independently from each other from the group H, OH, C$_1$-C$_8$ alkyl, C$_1$-C$_8$ alkoxy, C$_3$-C$_8$ cycloalkyl, C$_3$-C$_7$ aryl and C$_4$-C$_{15}$ aralkyl, optionally containing 1 to 4 heteroatoms selected from N, O and S in the chain or cycle, wherein the alkyl, cycloalkyl, aryl and aralkyl may be substituted by one or more substituents selected from the group OH, F, Cl, Br, I, CN, C$_1$-C$_4$ alkyl, C$_2$-C$_4$ alkenyl, C$_1$-C$_4$ alkoxy, C$_5$-C$_7$ aryl, C$_3$-C$_8$ cycloalkyl and C$_5$-C$_7$ aryloxy;

wherein alkyl, alkenyl, alkoxy, acyl, alkenyl, alkinyl and aralkyl may be present linear or branched;

and/or solvates, hydrates, esters, and pharmaceutically acceptable salts thereof.

In another preferred embodiment of the invention, the compound has one of the following formulae (Ia) to (Ic):

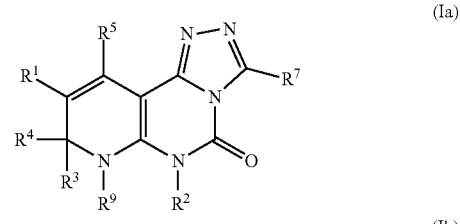

(Ia)

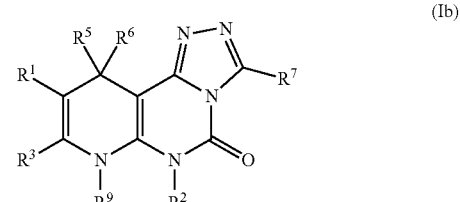

(Ib)

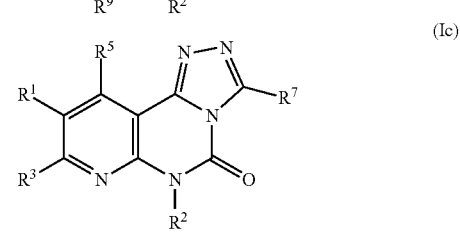

(Ic)

wherein R1 to R9 are defined as in claim 1.

Some of the compounds of the invention and/or salts or esters thereof will exist in different stereo isomeric forms. All of these forms are subjects of the invention.

Described below are exemplary salts of the compounds according to the invention which are included herein. The list of the different salts stated below is not meant to be complete and limiting.

Compounds according to the invention which contain one or more acidic groups can be used according to the invention, e.g. as their alkali metal salts, alkaline earth metal salts or ammonium salts. More precise examples of such salts include sodium salts, potassium salts, calcium salts, magnesium salts or salts with ammonia or organic amines such as, e.g. ethylamine, ethanolamine, triethanolamine or amino acids.

Compounds according to the invention which contain one or more basic groups, i.e. groups which can be protonated, can be used according to the invention in the form of their addition salts with inorganic or organic acids.

Examples for suitable acids include hydrogen chloride, hydrogen bromide, phosphoric acid, sulfuric acid, nitric acid, methanesulfonic acid, p-toluenesulfonic acid, napthalenedisulfonic acid, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to a person skilled in the art.

Compounds according to the invention which contain several basic groups can simultaneously form different salts.

If a compound according to the invention simultaneously contains acidic and basic groups in the molecule, the invention also includes, in addition to the salt forms mentioned, inner salts or betaines.

The respective salts of the compounds according to the invention can be obtained by customary methods which are known to the person skilled in the art, for example by contacting these with an organic or inorganic acid or base in a solvent or dispersant, or by anion exchange or cation exchange with other salts.

The term "pharmaceutically acceptable" means approved by a regulatory agency such as the EMEA (Europe) and/or the FDA (US) and/or any other national regulatory agency for use in animals, preferably in humans.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying Wnt signalling pathway modulating activity of a compound according of the invention in any suitable manner, such as any suitable in vitro assay.

The present invention furthermore includes all solvates of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention.

The present invention furthermore includes the metabolites of the compounds according to the invention.

The term "metabolites" refers to all molecules derived from any of the compounds according to the invention in a cell or organism, preferably mammal.

Preferably the term "metabolites" relates to molecules which differ from any molecule which is present in any such cell or organism under physiological conditions.

The structure of the metabolites of the compounds according to the invention will be obvious to any person skilled in the art, using the various appropriate methods.

The compounds according to general formula (I) and (Ia) to (Ic) can be prepared according to methods published in the literature or by analogous methods.

The compounds of the invention may be prepared according to the following scheme I:

Scheme 1

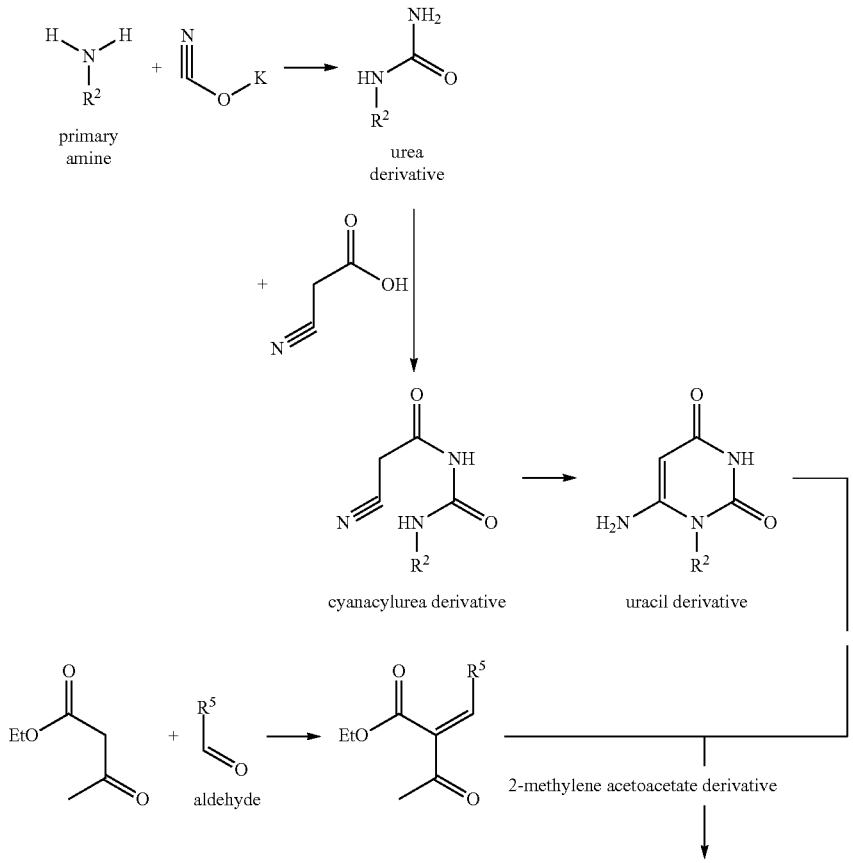

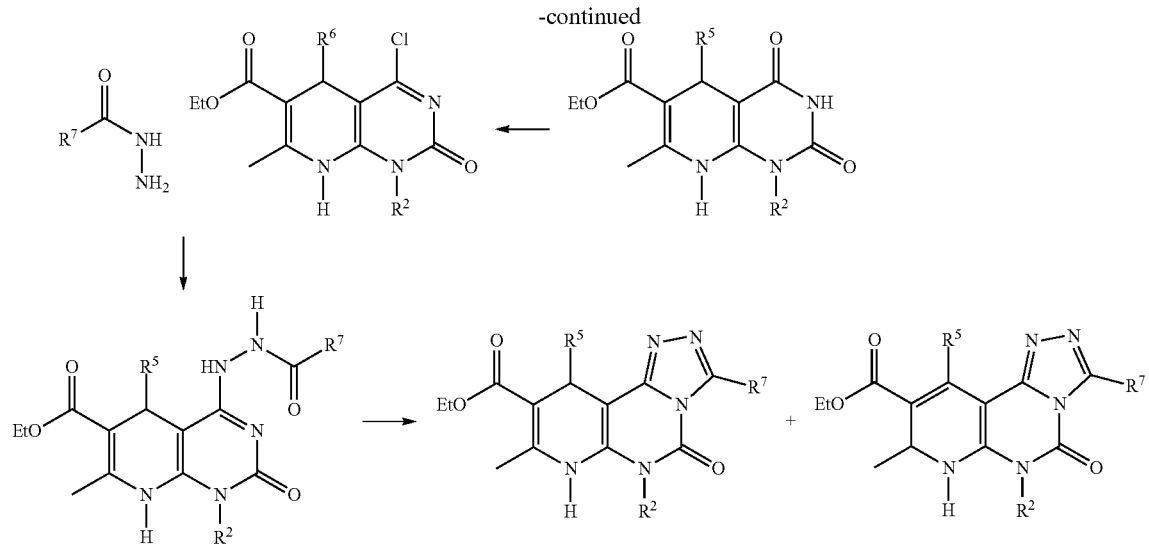

$R^2$, $R^5$ and $R^7$ in scheme 1 are defined as in formula I, Et: $CH_2CH_3$.

In an embodiment of the present invention the compounds of the invention may be prepared according to a process comprising the following steps:
a) reacting a primary amine with potassium cyanate, sodium cyanate or chlorosulfonylisocyanate to obtain an urea derivative,
b) reacting the urea derivative with cyan acetic acid to obtain the cyanacylurea derivative followed by intramolecular cyclisation to the 6-aminouracil derivative,
c) reacting an acetoacetate derivative with an aldehyde to obtain the 2-methylene acetoacetate derivative,
d) reacting the 6-aminouracil derivative from step b) and the 2-methylene acetoacetate derivative from step c) to obtain the 2,4-dioxohexahydropyrido[2,3-d]pyrimidine-6 carboxylic acid ethyl ester,
e) chlorination of 2,4-dioxohexahydropyrido[2,3-d]pyrimidine-6 carboxylic acid ethyl ester at C-4 to obtain 4-Chloro-7-methyl-2-oxo-tetrahydro-pyrido[2,3-d]pyrimidine-6-carboxylic acid ethyl ester, and
f) nucleophilic substitution of the chlorine at in 4-Chloro-7-methyl-2-oxo-tetrahydro-pyrido[2,3-d]pyrimidine-6-carboxylic acid ethyl ester with hydrazides followed by the ring closure.

"Primary amine" means $R—NH_2$ wherein R is defined as R1 in formula (I). Primary amines used for the preparation of the compounds of formula (I) and (Ia) to (If) are preferably selected from the group comprising ammonia, methylamine, 1-n-propyl amine, 2-n-propyl amine, cyclopropyl amine, 3-n-propylene amine, 2-amino ethanol, 2-amino ethylthiol, 2-amino dimethyl amine, N-2-amino-morpholine, 2-amino acetic acid, 3-amino propionic acid, 4-amino buntanoic acid, (D,L)-2-amino propionic acid, 2-amino ethansulfonic acid, aniline, m-amino phenol, p-amino benzoic acid amide, p-amino phenylsulfonic acid amide, 2-amino pyridine, 3-amino pyridine, 4-amino pyridine, 2-amino pyrimidine, 3-amino pyrazole, 3-amino-5-hydroxy pyrazole, 3-amino 1,2,4-triazol, lamino-1,2,4-triazol, 3-amino-5-thio-1,2,4-triazol, 3-amino isoxazole, 3-amino-5-methyl isoxazole, 5-amino-3-methyl isoxazole, 3,4-dimethyl-5-amino isoxazole, 4-amino-3-5-dimethyl isoxazole and 5-amino tetrazole, 2-aminothiadiazole, 2-amino-5-methylthiadiazole, 2-amino-5-ethylthiadiazole.

"aldehyde" means R—CHO wherein R is defined as R9 formula (I). Aldehydes used for the preparation of the compounds of formula (I) and (Ia) to (If) are preferably selected from the group comprising formaldehyde, acetaldehyde and substituted acetaldehydes, propionaldehyde and substituted propionaldehydes, N,N-dimethyl-2-amino acetaldehyde, acrylaldehyde, crotonaldehyde, benzaldehyde and substituted benzaldehydes, and furaldehyde and substituded furaldehydes, thiophenecarbaldehyde and substituted thiophenecarbaldehydes, Pyrrolecarboxaldehyde and substituted Pyrrolecarboxaldehydes, 1H-imidazolecarbaldehyde and substituted 1H-imidazolecarbaldehydes, 1H-pyrazolecarboxaldehyde and substituted 1H-pyrazolecarboxaldehydes, 1,2,4-Triazole-3-carboxaldehyde and substituted 1,2,4-Triazole-3-carboxaldehydes, Pyridinecarboxaldehyde and substituted Pyridinecarboxaldehydes.

"Substituted" means that the above mentioned aldehydes are substituted by one or more substituents as defined for R9 in formula (I).

Depending on the circumstances of the individual case, in order to avoid side reactions during the synthesis of a compound of the general formula (I) and (Ia) to (Ic), it can be necessary or advantageous to temporarily block functional groups by introducing protective groups and to deprotect them in a later stage of the synthesis, or to introduce functional groups in the form of precursor groups and at a later stage to convert them into the desired functional groups. Suitable synthetic strategies, protective groups and precursor groups are known to the person skilled in the art.

If desired, the compounds of the formulae (I) and (Ia) to (Ic) can be purified by customary purification procedures, for example by recrystallization or chromatography. The starting materials for the preparation of the compounds of the formula (I) and (Ia) to (Ic) are commercially available or can be prepared according to or analogously to literature procedures.

The compounds of the invention may serve as a basis for the preparation of the other compounds according to the invention by several methods well known by the person skilled in the art.

The present invention relates to the discovery that signal transduction pathways regulated by Wnt can be inhibited, at least in part, by compounds of formula (I). As set out in more detail below, these compounds can inhibit proliferation of tumor cells having Wnt modulated activity. Therefore, the compounds according to the invention are suited for modulating the Wnt signalling pathway.

As used herein, the term "modulating the Wnt signalling pathway" refers to an effect on the series of events that occur when Wnt proteins bind to cell-surface receptors of the frizzled family resulting in an accumulation of beta-catenin in the cell cytoplasm that reaches the nucleus of a cell, and consequently, the Wnt target genes are expressed. The Wnt signalling pathway may be modulated by direct or indirect modulation.

"Direct modulation" according to the present invention means an interaction of the inventive compounds with proteins directly involved in the Wnt signalling pathway leading to an increase or decrease of the expression of the Wnt target genes.

"Indirect modulation" according to the present invention means an increase or decrease of the expression of the Wnt target genes without a direct interaction of the inventive compound with the components involved in the Wnt signalling pathway. Examples for the indirect modulation of the Wnt signalling pathway are tankyrase-inhibitors and calcium regulators like siperone, thapsigargine and iononycine.

Inhibition of tankyrases stabilizes one protein of the Wnt signalling pathway (axin), which. inhibits the Wnt signalling pathway Inhibition of the decomposition of axin leads to an increase of axine and in turn to the inhibition of the Wnt signalling pathway (Huang et al., Nature 461, pp. 614 to 620 (2009))

By increasing the intracellular calcium level the Wnt protein beta-catenin is transferred out of the nucleus and decomposes. This inhibits a beta-catenin-mediated Wnt signalling pathway activity without inhibiting a Wnt protein directly, too ((Lu et al., BMC Pharm, 2009 9:13 (doi:10.1186/1471-2210-9-13) and L1 et al., PNAS 99, pp. 13254 to 13259 (2002)).

While not wishing to be bound by any particular theory, the activation of a receptor may be the mechanism by which these compounds act as described in US 2007/0219257 A1. For example, the compounds could affect the activity of a Wnt frizzled receptor. Alternatively, the compounds could affect the activity of the serine/threonine kinase GSK3β, which is involved in the down regulation of β-catenin. The compounds could also affect the activity of the APC gene. In the absence of Wnt signal, the APC protein functions to foster degradation of β-catenin and prevent its nuclear entry. Wnt stimulation, loss of APC protein function, or of its associated partner Axin, all lead to stabilization of and concentration in the nucleus of β-catenin, which then can act as a transcriptional co-activator by associating with the Tcf/LEF family of transcription factors. APC in complex with Axin and other proteins target β-catenin for proteasomal degradation by scaffolding the association between β-catenin and kinases whose action lead to β-catenin ubiquitinylation; this action is abrogated by recruitment of the degradation complex to the membrane upon Wnt activation of a receptor complex that includes Frizzled (Frz) and LRP5/6. The pathway can also be activated by mutations of β-catenin that render it resistant to degradation.

Or, for example, the compounds could alter the activity of Dishevelled, which is a positive mediator of Wnt signaling. For example, the ability of these compounds to inhibit proliferation of cells may be due to the ability of such molecules to interact with Wnt, or at least to interfere with the ability of those proteins to activate a Wnt-mediated signal transduction pathway. Signal transduction antagonists of different structures, even ones that bind to the same protein in the signaling pathways, may act in slightly different ways. Accordingly, even if a particular condition caused or contributed to by aberrant or unwanted activation of the Wnt pathway shows little response to treatment by one of the antagonists disclosed herein, another of the antagonists disclosed herein may nonetheless be efficacious.

One embodiment of the present invention includes the use of compounds of formula (I) that agonize inhibition of Wnt signaling, such as by inhibiting activation of Wnt downstream components of the signaling pathway, in the regulation of repair and/or functional performance of a wide range of cells, tissues and organs, including normal cells, tissues, and organs. For instance, the compounds of formula (I) have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the compounds of formula (I) can be applied to cells that are provided in culture (in vitro), or on cells in a whole animal (in vivo).

Another embodiment of present invention includes the use of compounds of formula (I), which antagonize activity of the Wnt pathway resulting in the regulation of repair and/or functional performance of a wide range of cells, tissues, and organs. For instance, the inventive compounds have therapeutic and cosmetic applications ranging from regulation of neural tissues, bone and cartilage formation and repair, regulation of spermatogenesis, regulation of smooth muscle, regulation of lung, liver and other organs arising from the primative gut, regulation of hematopoietic function, regulation of skin and hair growth, etc. The compounds of the invention can be applied on cells which are provided in culture (in vitro), or on cells in a whole animal (in vivo).

The term "agonist" refers to an agent or analog that binds productively to a receptor and mimics its biological activity. The term "antagonist" refers to an agent that binds to receptors but does not provoke the normal biological response. Thus, an antagonist potentiates or recapitulates, for example, the bioactivity of patched, such as to repress transcription of target genes. The term "Wnt antagonist" as used herein refers not only to any agent that may act by directly inhibiting the normal function of the Wnt protein, but also to any agent that inhibits the Wnt signaling pathway, and thus recapitulates the function of Wnt. The term "Wnt agonist" likewise refers to an agent which antagonizes or blocks the bioactivity of Wnt, such as to increase transcription of target genes.

It is preferred according to the invention to decrease the activity of the Wnt signalling pathway and/or to inhibit the Wnt signalling pathway. Preferably the compounds of the invention are used as Wnt antagonists and used to regulate e.g. proliferation or other biological consequences of misexpression of Wnt.

As outlined above, an elevated Tcf-beta-catenin level in the nucleus of a cell is a hallmark of an aberrant activation of the Wnt signalling pathway and plays a major role in the development of several kinds of cancer. The measurement of the Tcf-beta-catenin level in the nucleus of the cell may be carried out according procedures known to the person skilled in the art. The measurement of the Tcf-beta-catenin level by means of 6×TcF-luciferase is described below in the experiments. The use of a compound for modulating the Wnt signalling pathway resulting in a decrease of the relative amount of Tcf-beta-catenin complex in the nucleus of a cell is preferred.

Modulating the Wnt signalling pathway can be carried out by contacting a cell with a compound according to the invention. In one embodiment of the invention, said modulation is performed in vitro or in cell culture. As known to the person skilled in the art, several in vitro and cell culture assays are available.

According to a further embodiment of the invention the modulation can be performed in animals such as mammals. Animal subjects to which the invention is applicable extend to both domestic animals and livestock, raised either as pets or for commercial purposes. Exemplary mammals are mice, rats, guinea pigs, monkeys, dogs and cats. The modulation can also be carried out in humans.

The invention also relates to the compounds of the invention for use as a medicament. The compounds are as defined above; furthermore the embodiments as described below with respect to the use as medicament, e.g. formulation, application and combination, also apply to this aspect of the invention. The pharmaceutical preparation or medicaments comprising the compounds of formula (I) can be effective for both human and animal subjects. Animal subjects to which the invention is applicable extend to both domestic animals and livestock, raised either as pets or for commercial purposes. Examples are dogs, cats, cattle, horses, sheep, hogs, and goats.

The compounds according to the invention are suited for the use for the preparation of a medicament for modulating the Wnt signalling pathway. The present invention provides pharmaceutical preparations or medicaments comprising a compound such as described herein, formulated in an amount sufficient to regulate, in vivo, Wnt pathway, e.g., proliferation or other biological consequences of mis-expression of Wnt.

The invention further relates to the use of a compound according to the invention for the preparation of a medicament for the treatment of a disorder or disease associated with an aberrant activation of Wnt signalling in a mammal. The disorders or diseases associated with the Wnt signalling pathway are for example cell-proliferative disorders, rheumatoid arthritis, diseases connected with aberrant bone density and Dupuytren disease (superficial fibromatosis).

A cell proliferation disorder is a disorder which is connected with some degree of abnormal cell proliferation. Especially, cell-proliferation disorders are important for the development of cancer. A further cell-proliferation disorder is proliferative skin disorders which are marked by unwanted or aberrant proliferation of cutaneous tissue, for example X-linked ichtyosis, psoriasis, atopic dermatitis, allergic contact dermatitis, epidermolytic hyperkeratosis and seborrheic dermatitis. In one preferred aspect, the invention relates to the use of the compounds according to the invention for the preparation of a medicament for the treatment of cancer or proliferative skin disorder.

The Wnt-signalling pathway is also believed to be involved in the maintenance of stem or progenitor cells in a growing list of adult tissues that includes e.g. skin, blood, gut, prostate, muscle and the nervous system. Stem and progenitor cells are important for cell regeneration and consequently for aging and aging related processes. Therefore, the compounds of the invention are useable for the preparation of a medicament for the treatment of aging and age-related disorders and/or diseases.

The compounds of the invention are especially suitable for the use for the preparation of a medicament for the treatment of cancer wherein the cancer is a member of the group multiple myeloma, colon cancer, breast cancer, gastric cancer, colorectal cancer, lung cancer, prostate cancer, ovarian cancer, bladder cancer, liver cancer, uterine cancer, kidney cancer, leukaemia, gliomas, basal cell carcinoma, rhabdomyosarcoma, mesothelioma, osteosarcoma, medulloblastomas and other primary CNS malignant neuroectodermal tumors.

Possible disorders or diseases which may be treated by administering a medicament prepared from the compounds for formula (I) including formulae (Ia) to (If) are described in detail in US 2007/0219257 A1. Accordingly the compounds of the present invention are applicable to cell culture techniques wherein, whether for genetic or biochemical reasons, the cells have a Wnt receptor. Alternatively, a compound of formula (I) may be employed in a related method directed towards cells which have a Wnt receptor. In vitro neuronal culture systems have proven to be fundamental and indispensable tools for the study of neural development, as well as the identification of neurotrophic factors such as nerve growth factor (NGF), ciliary trophic factors (CNTF), and brain derived neurotrophic factor (BDNF). One use of the compounds of formula (I) may be in cultures of neuronal stem cells, such as in the use of such cultures for the generation of new neurons and glia. In such embodiments of the subject method, the cultured cells can be contacted with an aromatic compound of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motor-neurons: Such neuronal cultures can be used as convenient assay systems as well as sources of implantable cells for therapeutic treatments.

In another embodiment, the compounds of the invention can be used in the treatment of neoplastic or hyperplastic transformations such as may occur in the central nervous system. For instance, the compounds can be utilized to cause such transformed cells to become either post-mitotic or apoptotic. The compounds may, therefore, be used as part of a treatment for, e.g., malignant gliomas, meningiomas, medulloblastomas, neuroectodermal tumors, and ependymomas.

In another embodiment, the compounds of the invention can be used as part of a treatment regimen for malignant medulloblastoma and other primary CNS malignant neuroectodermal tumors.

In certain embodiments, the compounds of the invention are used as part of treatment program for medulloblastoma. Medulloblastoma, a primary brain tumor, is the most common brain tumor in children. A medulloblastoma is a primitive neuroectodermal tumor (PNET) arising in the posterior fossa. Histologically, they are small round cell tumors commonly arranged in true rosettes, but may display some differentiation to astrocytes, ependymal cells or neurons. PNET's may arise in other areas of the brain including the pineal gland (pineoblastoma) and cerebrum.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the compounds of formula (I) are used as part of a treatment program for hepatocellular carcinoma. Hepatocellular carcinoma is a form of cancer that arises from hepatocytes, the major cell type of the live, and is one of the most common tumors involving mutations in the Wnt pathway.

In other embodiments, the compounds of formula (I) are used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes.

Yet another aspect of the present invention concerns the observation in the art that Wnt is involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising one or more of the inventive compounds can also be utilized for both cell culture and therapeutic uses involving generation and maintenance of non-neuronal tissue.

In one embodiment, the present invention makes use of the discovery that Wnt is apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, compounds of formula (I) can be employed for regulating the development and maintenance of an artificial liver which can have multiple metabolic functions of a normal liver. In an exemplary embodiment, the compounds of formula (I) can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of inventive compounds can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the compounds of formula (I) can be employed therapeutically to regulate such organs after physical, chemical or pathological insult. For instance, therapeutic compositions comprising the compounds of formula (I) can be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al., Curr. Biol. 7:801-4 (1997). The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialised mesoderm derivatives of the small intestine and pancreas. To test this, they used the promoter of the Ipf1/Pdx1 gene to selectively express Shh in the developing pancreatic epithelium. In Ipf1/Pdxl-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the inventive compounds can be used to control or regulate the proliferation and/or differentiation of pancreatic tissue both in vivo and in vitro.

There are a wide variety of pathological cell pro-liferative and differentiative conditions for which the compounds of the present invention may provide therapeutic benefits, with the general strategy being, for example, the correction of aberrant insulin expression, or modulation of differentiation. More generally, however, the present invention relates to the use of the compounds of formula (I) for inducing and/or maintaining a differentiated state, enhancing survival and/or affecting proliferation of pancreatic cells, by contacting the cells with the subject inhibitors. For instance, it is contemplated by the invention that, in light of the apparent involvement of Wnt in the formation of ordered spatial arrangements of pancreatic tissues, the compounds of the invention could be used as part of a technique to generate and/or maintain such tissue both in vitro and in vivo. For instance, modulation of the function of Wnt can be employed in both cell culture and therapeutic uses involving generation and maintenance B-cells and possibly also for non-pancreatic tissue, such as in controlling the development and maintenance of tissue from the digestive tract, spleen, lungs, colon, and other organs which derive from the primitive gut.

In an exemplary embodiment, the compounds of the invention can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of B-cells or decreased islet cell mass. To the extent that aberrant Wnt signaling may be indicated in disease progression, the compounds of the invention can be used to enhance regeneration of the tissue after anti-tumor therapy.

Moreover, manipulation of Wnt signaling properties at different points may be useful as part of a strategy for reshaping/repairing pancreatic tissue both in vivo and in vitro. In one embodiment, the present invention makes use of the apparent involvement of Wnt in regulating the development of pancreatic tissue. In general, the compounds of the invention can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering Wnt, can provide a means for more carefully controlling the characteristics of a cultured tissue. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature B-cells can be observed. By utilizing the compounds of the invention, the differentiation path or pro-liferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of Wnt function to affect tissue differentiation can be utilized as a means of maintaining graft viability.

Bellusci et al., Development 124:53 (1997) report that Sonic hedgehog regulates lung mesenchymal cell proliferation in vivo. Accordingly, the compounds of the invention can be used to regulate regeneration of lung tissue, e.g., in the treatment of emphysema.

Fujita et al., Biochem. Biophys. Res. Commun. 238:658 (1997) reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that ptc and/or Wnt is involved in the cell growth of such transformed lung tissue and therefore indicates that the compounds of the invention can be used as part of a treatment of lung carcinoma and adenocarcinomas, and other proliferative disorders involving the lung epithelia.

Many other tumors may, based on evidence such as involvement of the Wnt pathway in these tumors, or detected expression of Wnt or its receptors in these tissues during development, be affected by treatment with the compounds of the invention. Such tumors include, but are by no means limited to, tumors related to Gorlin's syndrome (e.g., basal cell carcinoma, medulloblastoma, meningioma, etc.), tumors evidenced in pet knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chon-drosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

In still another embodiment of the present invention, compositions comprising one or more of the compounds of the invention can be used in the in vitro generation of skeletal tissue, such as from skeletogenic stem cells, as well as the in vivo treatment of skeletal tissue deficiencies. The present invention particularly contemplates the use of compounds of the invention to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the compounds of the invention can be used as part of a regimen for restoring cartilage function to a connective tissue. They are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The compounds of the invention may also be useful for remodeling cartilage matrix, such as in plastic or reconstructive surgery, as well as periodontal surgery. They may also be applied to improving a previous reparative procedure, for example, following surgical repair of a meniscus, ligament, or cartilage. Furthermore, it may prevent the onset or exacerbation of degenerative disease if applied early enough after trauma.

One embodiment of the present invention relates to the treating of the afflicted connective tissue with a therapeutically effective amount of compounds of the invention to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the compounds of the invention can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the compounds of the invention can be used to treat a degenerative disorder of a knee, such as which might be the result of traumatic injury (e.g., a sports injury or excessive wear) or osteoarthritis. The compounds of the invention may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the compounds of the invention in the field of cartilage transplantation and prosthetic device therapies. However, problems arise, for instance, because the characteristics of cartilage and fibrocartilage vary between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the compounds of the invention can be used to particularly address this problem, by helping to adaptively control the implanted cells in the new environment and effectively resemble hypertrophic chondrocytes of an earlier developmental stage of the tissue.

In similar fashion, the compounds of the invention can be applied to enhancing both the generation of prosthetic cartilage devices and to their implantation. The need for improved treatment has motivated research aimed at creating new cartilage that is based on collagen-glycosaminoglycan templates (Stone et al., Clin. Orthop. Relat. Red 252:129 (1990)), isolated chondrocytes (Grande et al., J. Orthop. Res. 7:208 (1989); and Takigawa et al., Bone Miner 2:449 (1987)), and chondrocytes attached to natural or synthetic polymers (Walitani et al., J. Bone Jt. Surg. 71B:74 (1989); Vacanti et al., Plast. Reconstr. Surg. 88:753 (1991); von Schroeder et al. J. Biomed. Mater. Res. 25:329 (1991); Freed et al., J. Biomed.

Mater. Res. 27:11 (1993); and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the invention, the implants are contacted with a subject aromatic compound during certain stages of the culturing process in order to manage the rate of differentiation of chondrocytes and the formation of hypertrophic chrondrocytes in the culture.

In another embodiment, the implanted device is treated with a compound of formula (I) in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the compounds of the invention are used to enhance attachment of prosthetic devices. To illustrate, the compounds of the invention can be used in the implantation of a periodontal prosthesis, wherein the treatment of the surrounding connective tissue stimulates formation of periodontal ligament about the prosthesis.

In other embodiments, the compounds of the invention can be employed as part of a regimen for the generation of bone (osteogenesis) at a site in the animal where such skeletal tissue is deficient. Indian hedgehog (Ihh) is particularly associated with the hypertrophic chondrocytes that are ultimately replaced by osteoblasts. For instance, administration of a compound of the present invention can be employed as part of a method for regulating the rate of bone loss in a subject. For example, preparations comprising subject compounds can be employed, for example, to control endoch-ondral ossification in the formation of a "model" for ossification.

The compounds of the invention also have wide applicability to the treatment or prophylaxis of disorders afflicting epithelial tissue, as well as in cosmetic uses. In general, this includes a step of administering to an animal an amount of a subject aromatic compound effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the compounds of the invention, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, a lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of a compound of formula (I) can reduce the abnormal proliferation and differentiation of the affected epithelium, helping to reduce the severity of subsequent inflammatory events.

The compounds of the invention and compositions thereof can also be used to treat wounds resulting from dermatological diseases, such as lesions resulting from autoimmune disorders such as psoriasis. Atopic dermititis refers to skin trauma resulting from allergies associated with an immune response caused by allergens such as pollens, foods, dander, insect venoms and plant toxins.

In other embodiments, antiproliferative preparations of subject compounds can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intra-capsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the present invention provides a means for inhibiting proliferation of the remaining lens epithelial cells. For example, such cells can be induced to remain quiescent by instilling a solution containing a preparation of a compound of formula (I) into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The compounds of the invention can also be used in the treatment of corneopathies marked by corneal epithelial cell proliferation, as for example in ocular epithelial disorders such as epithelial downgrowth or squamous cell carcinomas of the ocular surface.

Yet another aspect of the present invention relates to the use of the compounds of the invention to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the compounds of the invention can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, subject compounds can be used to manage hirsutism, a disorder marked by abnormal hairiness. The compounds of the invention can also provide a process for extending the duration of depilation.

Moreover, because a subject compound will often be cytostatic to epithelial; cells, rather than cytotoxic, such agents can be used to protect hair follicle cells from cytotoxic agents which require progression into S-phase of the cell-cycle for efficacy, e.g. radiation-induced death. Treatment by the compounds of the invention can provide protection by causing the hair follicle cells to become quiescent, e.g., by inhibiting the cells from entering S phase, and thereby preventing the follicle cells from undergoing mitotic catastrophe or programmed cell death. For instance, compounds of the invention can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, the administration of compounds of the invention can be stopped with concomitant relief of the inhibition of follicle cell proliferation.

The compounds of the invention can also be used in the treatment of folliculitis, such as folliculitis decalvans, folliculitis ulerythematosa reticulata or keloid folliculitis. For example, a cosmetic preparation of a compound of formula (I) can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the compounds of the invention can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The compounds of the invention can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of an inventive compound, e.g., which promotes quiescense or differentiation, can be used to treat varying forms of psoriasis, be they cutaneous, mucosal orungual. Psoriasis, as described above, is typically characterized by epidermal keratinocytes which display marked proliferative activation and differentiation along a "regenerative" pathway. Treatment with an antipro-liferative compound of the invention can be used to reverse the pathological epidermal activiation and can provide a basis for sustained remission of the disease.

A variety of other keratotic lesions are also candidates for treatment with the compounds of the invention. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a composition containing at least one compound of formula (I) in amounts sufficient to inhibit hyperproliferation of epidermal/epidermoid cells of the lesion.

Acne represents yet another dermatologic ailment which may be treated by the compounds of the invention. Acne vulgaris, for instance, is a multifactorial disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by Propinobac-terium acnes and *Staphylococcus epidermidis* bacteria and Pitrosporum ovale, a yeast. Treatment with an antiproliferative compound of formula (I), particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions which are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The compounds of the invention can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the compounds of the invention can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

Ailments which may be treated by the compounds of the invention are disorders specific to non-humans, such as mange.

In still another embodiment, the compounds of the invention can be used in the treatment of human cancers, particularly basal cell carcinomas and other tumors of epithelial tissues such as the skin. For example, compounds of the invention can be employed, in the subject method, as part of a treatment for basal cell nevus syndrome (BCNS), and other other human carcinomas, adenocarcinomas, sarcomas and the like.

In another embodiment, the compounds of the invention are used as part of a treatment of prophylaxis regimen for treating (or preventing) basal cell carcinoma. The deregulation of the Wnt signaling pathway may be a general feature of basal cell carcinomas caused by ptc mutations. Consistent over expression of human ptc mRNA has been described in tumors of familial and sporadic BCCs, determined by in situ hybridization. Mutations that inactivate ptc may be expected to result in over expression of mutant Ptc, because ptc displays negative autoregulation. Likewise, mutations that inactivate Wnt may be expected to result in overexpression of mutant Wnt, because Wnt displays negative autoregulation. Prior research demonstrates that overexpression of hedgehog proteins can also lead to tumorigenesis. That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Wnt, Shh or other Hh genes in humans could act as dominant oncogenes in humans. Sporadic ptc mutations have also been observed in BCCs from otherwise normal individuals, some of which are UV-signature mutations. In one recent study of sporadic BCCs, five UV-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al., Science 277:1109-13 (1997); Xie et al. Cancer Res. 57:2369-72 (1997); Oro et al. Science 276:817-21 (1997); Xie et al, Genes Chromosomes Cancer 18:305-9 (1997); Stone et al, Nature 384:129-34 (1996); and Johnson et al. Science 272:1668-71 (1996).

The compounds of the invention can also be used to treat patients with BCNS, e.g., to prevent BCC or other effects of the disease which may be the result of Wnt-mediated disorders. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyl), syndactyl), and spina bifida. They also develop a number of tumor types in addition to BCCs: fibromas of the ovaries and heart, cysts of the skin and jaws, and in the central nervous system, medulloblas-tomas and meningiomas. The compounds of the invention can be used to prevent or treat such tumor types in BCNS and non-BCNS patients. Studies of BCNS patients show that they have both genomic and sporadic mutations in the ptc gene, suggesting that these mutations are the ultimate cause of this disease.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety hyperplastic or neoplastic conditions affecting platelets.

Furthermore, the invention relates to pharmaceutical compositions comprising at least one compound according to the invention. In a preferred embodiment, the invention relates to pharmaceutical compositions comprising at least one compound according to the invention in a mixture with an inert carrier, where said inert carrier is a pharmaceutical carrier.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The invention further relates to a method for the preparation of a medicament comprising the steps of:
a) preparing at least one compound according to the formulae (I) and (Ia) to (Ic); and
b) formulating a medicament containing said compound; and to a method of treating a mammal for the modulation of the Wnt signalling pathway wherein the method comprises administering to said mammal a therapeutically effective amount of a compound according to formula (I) and (Ia) to (Ic).

The compounds according to the invention used for the preparation of a medicament for the modulation of the Wnt signalling pathway in a mammal may be administered in any convenient route. The compounds are formulated to be compatible with the desired route of administration and may be administered together with other biologically active agents.

The compounds may be formulated for the intravenous, intradermal, subcutanus, intramuscular, intraperitoneal, epidural, oral, transdermal, transmucosal, rectal or pulmonary administration. Administration can be systemic or local. Pulmonary administration can be employed by use of an inhaler or nebulizer, and formulation with an aerosolizing agent, for example. In another embodiment, the compound can be delivered in a vesicle, in particular a liposome (Langer (1990) Science 249, 1527.

In yet another embodiment, the compound can be delivered via a controlled release system. In one embodiment, a pump may be used (Sefton (1987) CRC Crit. Ref. Biomed. Eng. 14, 201; Buchwald et al. (1980) Surgery 88, 507; Saudek et al. (1989) N. Engl. J. Med. 321, 574). In another embodiment, polymeric materials can be used (Ranger and Peppas (1983) Macromol. Sci. Rev. Macromol. Chem. 23, 61; Levy et al. (1985) Science 228, 190; During et al. (1989) Ann. Neurol. 25, 351; Howard et al. (1989) J. Neurosurg. 71, 858). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115). Other controlled release systems are discussed in the review by Langer (1990, Science 249, 1527).

Toxicity and therapeutic efficacy of the compounds of the invention can be determined by standard pharmaceutical procedures in cell cultures or experimental animals. The results obtained from the cell culture assays and animal studies can be used in formulating the range of dosage for use in medicaments in humans. The specific dosage for any particular subject is influenced by several factors, e.g. by the activity of the specific compound used, the age, body weight, general health, gender and diet of the subject, the time and the route of administration and the rate of excretion.

EXAMPLES

Examples 15 and 16

Step 1: Synthesis of N-Phenylurea

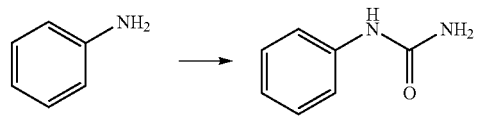 [SMILES: Nc1ccccc1 ; NC(=O)Nc1ccccc1]

Aniline (18.6 g, 200 mmol) was dissolved in 100 ml of 2M hydrochloric acid (aq.), cooled down to 2° C. by immersing in ice bath, charged with potassium cyanate (19.5 g, 240 mmol) portion wise in 30 minutes under stirring, the cooling was removed and stirred for 4 h at room temperature, whereby thick white solids precipitated. The reaction mixture was stored at 4° C. for 1 h. The solids were separated by filtration, washed well with ice cold water and dried under vacuum yielding pure white solids (25.6 g, 94%).

Step 2: Synthesis of
1-(2-Cyano-acetyl)-3-phenyl-urea

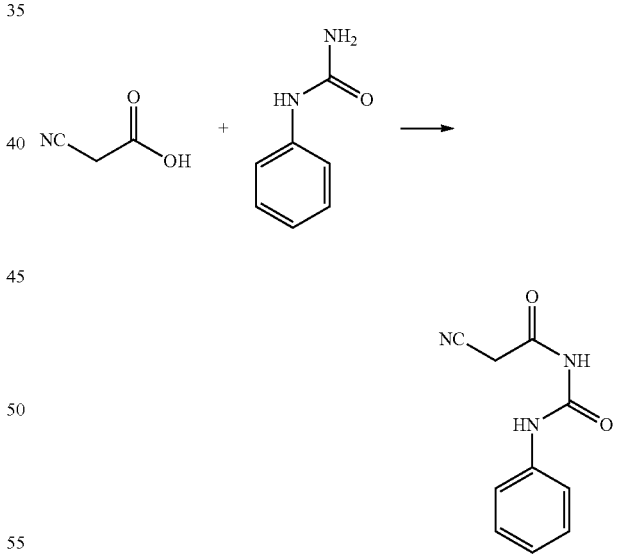

Cyanoacetic acid (28 g, 340 mmol) was taken in 20 ml acetic acid and 40 ml acetic anhydride (400 mmol), stirred at 50° C. until all cyanoacetic acid was solved. Phenyl urea (33.05 g, 247.5 mmol) was added and the mixture was stirred at 95° C. for 60 minute under LC-MS (Liquid Chromatography coupled with Mess Spectrometer) control of the reaction progress. After cooling down to room temperature, dilution with 20 ml 2-propanol and storing at 4° C. for 2 h, solids were separated by filtration, washed with cold 2-propanol and dried under high vacuum giving 40.06 g of white solids (82.6%).

Step 3: Synthesis of 6-Amino-1-phenyl-1H-pyrimidine-2,4-dione

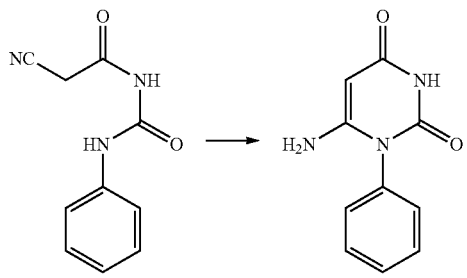 [SMILES: N#CCC(=O)NC(=O)Nc1ccccc1 ; Nc1cc(=O)[nH]c(=O)n1-c1ccccc1]

1-(2-Cyano-acetyl)-3-phenyl-urea (12.6 g, 62.1 mmol) was taken in 50 ml 2M sodium hydroxide (aq.) and stirred at room temperature for 2 h under LC-MS control. After cooling down by immersing in ice bath and neutralization with acetic acid and thus formed solids were separated by filtration, washed well with ice cold water and dried under high vacuum yielding white solids (11.9 g, 58.6 mmol, 94.4%).

Step 4: Synthesis of 2-benzylidene acetoacetate

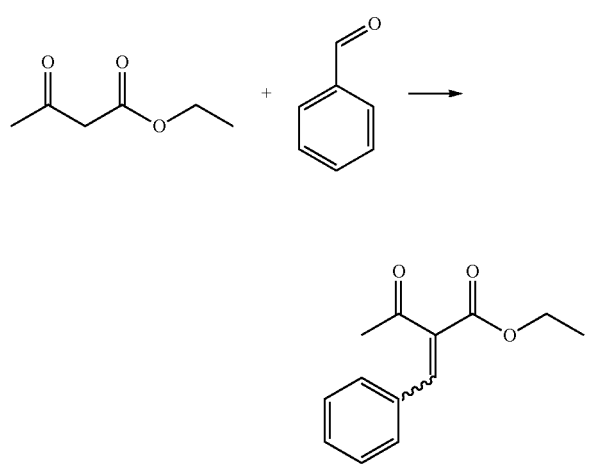

Benzaldehyde (10.6 g, 100 mmol), ethyl acetoacetate (16.9 g, 130 mmol), acetic acid (1 ml) and piperidine (1.2 ml) were taken in dry toluene (20 ml) with Molecular sieve (4 g, 4 A) and stirred at room temperature for 19 h under LC-MS control, whereby the reaction went to completion. The reaction mixture was diluted with 20 ml cyclohexane, washed successively with water, 2M sodium hydroxide (aq), 1M hydrochloric acid (aq) and brine and then dried over magnesium sulfate. The solvent was then evaporated and the residue dried under high vacuum yielding a light yellow oil (18.3 g, 84%).

Step 5: Synthesis of 7-Methyl-2,4-dioxo-1,5-diphenyl-1,2,3,4,5,8-hexahydro-pyrido[2,3-d]pyrimidine-6-carboxylic acid ethyl ester

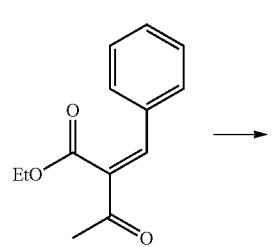

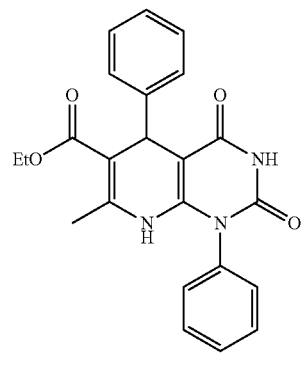

(1)

6-Amino-1-phenyl-uracil (30.5 g, 150 mmol), 2-benzylidene acetoacetate (39.5 g, 180 mmol) were taken in 150 ml 2-ethoxyethanol with calcium chloride (20 g) and stirred at 90° C. for 24 h under LC-MS control. The reaction mixture was cooled down to room temperature and stored at 4° C. for 2 h. The solids were separated by filtration, washed with ice cold 2-propanol and dried under high vacuum yielding pure white solids (36.3 g, 95 mmol, 63%).

Step 6: Synthesis of 4-Chloro-7-methyl-2-oxo-1,5-diphenyl-1,2,5,8-tetrahydro-pyrido[2,3-d]pyrimidine-6-carboxylic acid ethyl ester

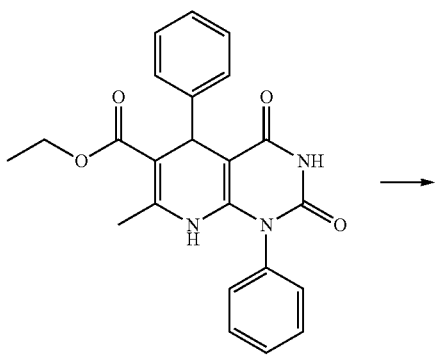

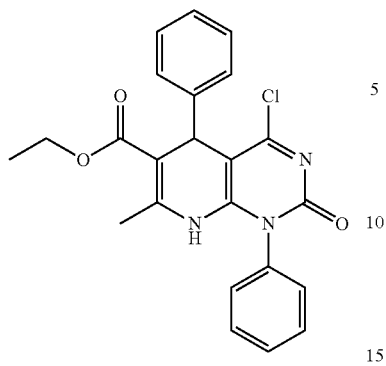

The compound from step 5 (11 g, 27.3 mmol) was taken in 100 ml dry chloroform and then charged with DMF (dimethylformamide) (2 ml, 27 mmol). POCl₃ (14 ml) was dissolved in advance in 26 ml chloroform and was added under stirring in an argon atmosphere. The reaction mixture was then stirred at 70 C for 6 h. The reaction was monitored by LC-MS. The reaction mixture was cooled down to room temperature and poured into 25% ice cold solution of potassium acetate (150 ml) under vigorous stirring, organic phase was separated, aqueous phase was extracted with DCM (dichloromethane) (2×100 ml) and the combined organic solution was dried over magnesium sulfate and then the solvent was evaporated under vacuum yielding yellow solids (8.3 g, 19.7 mmol, 72%).

Step 7: Synthesis of 4-[N-(3-Methoxy-benzoyl)-hydrazino]-7-methyl-2-oxo-1,5-diphenyl-1,2,5,8-tetrahydro-pyrido[2,3-d]pyrimidine-6-carboxylic acid ethyl ester

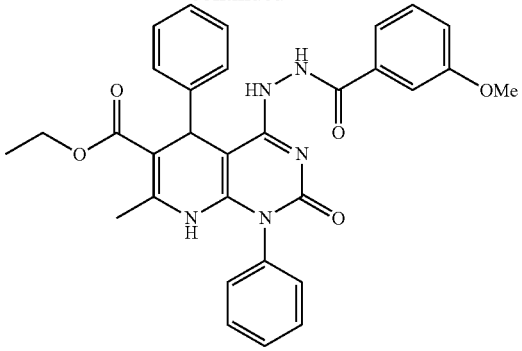

The compound of step 6 (100 mg, 0.237 mmol) was taken in 2 ml EtOH and treated successively with m-anisic hydrazide (99.6 mg, 0.6 mmol) and TEA (Triethylamine) (35 microl, 0.25 mmol) at room temperature and stirred at 60° C. for 72 h.

The reaction mixture was partitioned between water (25 ml) and DCM (30 ml). The organic phase was separated and the solvent was evaporated under vacuum at 40° C. The product was purified with HPLC on a RP-18 column (Sphinx, 21 mm×250 mm, 5 microm, Macherey-Nagel) with a gradient 30-100% MeCN with 0.02% HCOOH in 22 min and a flow rate of 21 ml/min yielding a light yellow solid (85.5 mg, 0.155 mmol, 65.4%).

Step 8: Synthesis of 3-(3-Methoxy-phenyl)-7-methyl-4-oxo-5,9-diphenyl-4,5,6,9-tetrahydro-1,2,3a,5,6-pentaaza-cyclopenta[a]naphthalene-8-carboxylic acid ethyl ester and 3-(3-Methoxy-phenyl)-7-methyl-4-oxo-5,9-diphenyl-4,5,6,7-tetrahydro-1,2,3a,5,6-pentaaza-cyclopenta[a]naphthalene-8-carboxylic acid ethyl ester

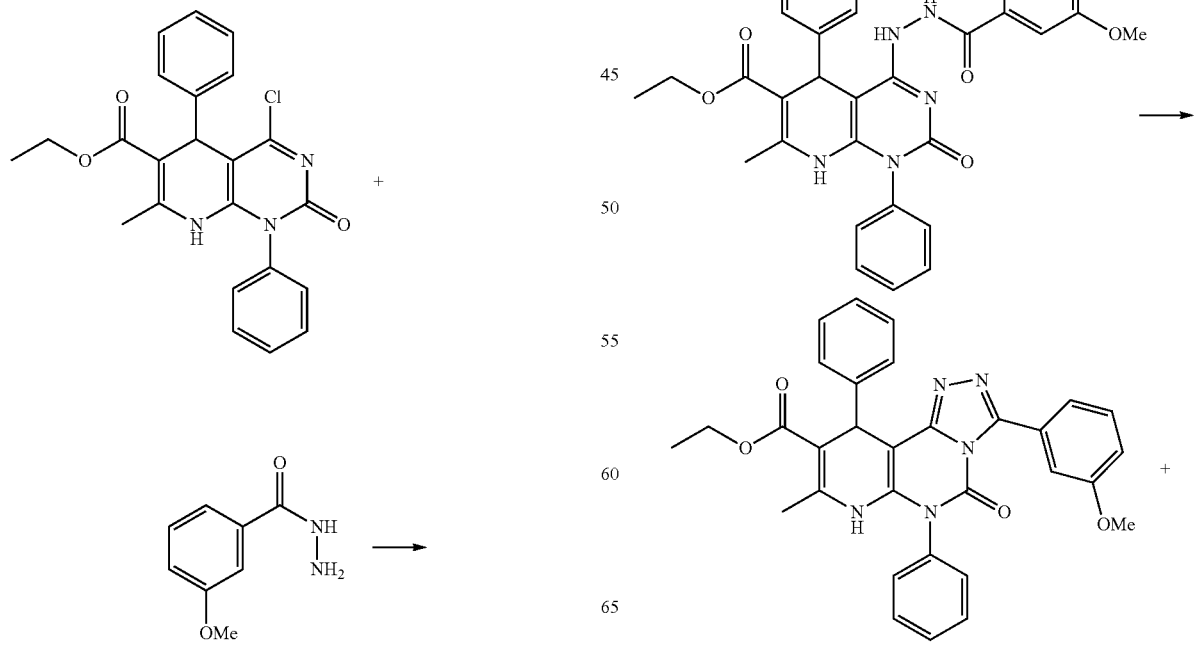

-continued

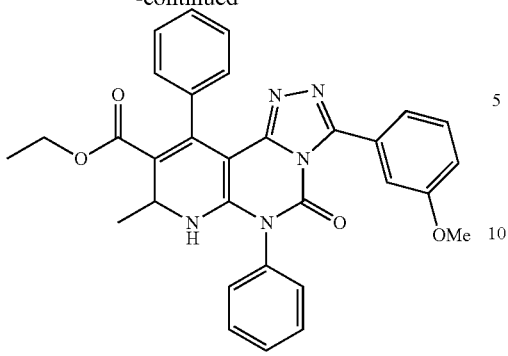

The compound of step 7 (52 mg, 100 umol) was taken in 2 ml acetic acid under argon atmosphere and stirred at 80° C. for 48 h. The solvent was removed under vacuum at 30° C. from the reaction mixture. The product was purified with HPLC on a RP-18 column (Sphinx, 21 mm×250 mm, 5 microm, Macherey-Nagel) with a gradient 5-100% MeCN with 0.02% HCOOH in 22 min and a flow rate of 21 ml/min yielding a white solid (H1=16.6 mg and H2=11.7 mg).

Examples 1 to 14 and 17 to 22 were prepared in analogy to examples 15 and 16 using the respective hydrazide (R5-CO—NH—NH$_2$) instead of anisic hydrazide in step 7 of the synthesis, i.e. R5 is 4-pyridiyl (ex. 1 and 2), benzyl (ex. 3), 2-furanyl (ex 4 and 5), p-amino phenyl (ex. 6 and 7), 3-pyridyl (ex. 8 and 9), methyl (es. 10), p-F-phenyl (es. 11 and 12), p-hydroxyphenyl (ex. 13 and 14), p-methoxy phenyl (ex. 17 and 18), 2-thiophenyl (ex. 19 and 20) and phenyl (ex. 21 and 22).

Examples 23 to 34 were prepared from the respective examples 1 to 23 by oxidation with DDQ (2,3-dichloro-5,6-dicyanobenzoquinone) according to the following method: The compound was taken in 1 ml DCM, charged with 0.1M ethanolic solution of DDQ (1.05 eqv.) and then stirred at room temperature for approximately 2 h. The reaction mixture was diluted with DCM to about 10 ml, washed successively with 5% sodium bicabonate (10 ml) and with brine (10 ml). Afterwards the solvent was evaporated under vacuum. The product was purified with HPLC on a RP-18 column (Sphinx, 21 mm×250 mm, 5 microm, Macherey-Nagel) with a gradient 5-100% MeCN with 0.02% HCOOH in 22 min and a flow rate of 21 ml/min yielding the solid product.

The structures of examples 1 to 34 are shown in table 1.

TABLE 1

| Example | Structure |
|---|---|
| 1 | 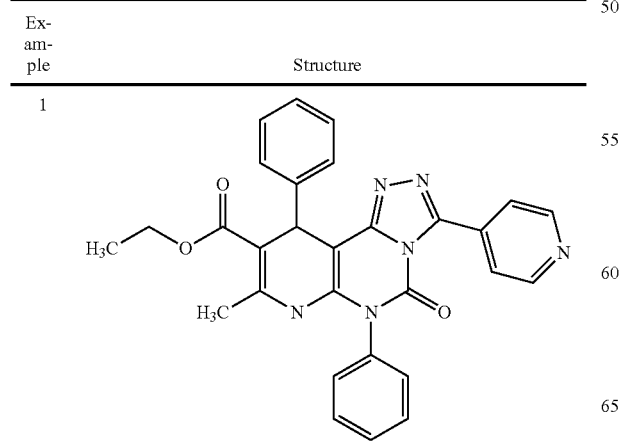 |
| 2 | 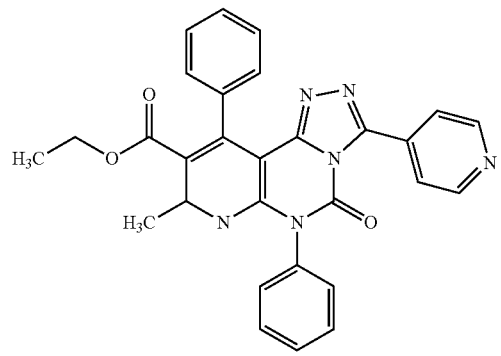 [SMILES: CCOC(=O)C1=C(c2ccccc2)c2c(n(-c3ccccc3)c(=O)n3c(-c4ccncc4)nnc23)NC1C] |
| 3 | 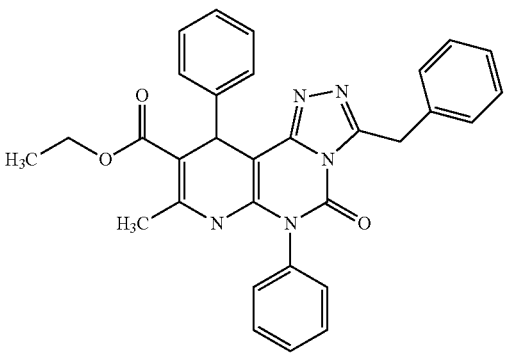 [SMILES: CCOC(=O)C1=C(C)Nc2c(c3nnc(Cc4ccccc4)n3c(=O)n2-c2ccccc2)C1c1ccccc1] |
| 4 | 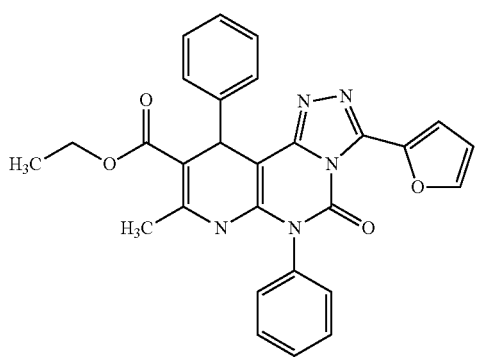 |
| 5 | 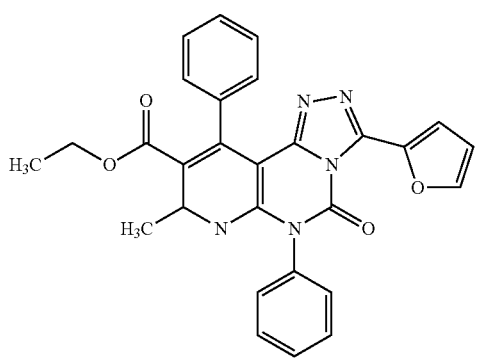 [SMILES: CCOC(=O)C1=C(c2ccccc2)c2c(n(-c3ccccc3)c(=O)n3c(-c4ccco4)nnc23)NC1C] |

TABLE 1-continued
| Example | Structure |
|---|---|
| 6 | 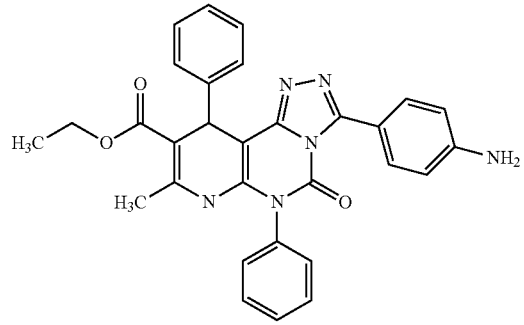 [SMILES: CCOC(=O)C1=C(C)Nc2c(c3nnc(-c4ccc(N)cc4)n3c(=O)n2-c2ccccc2)C1c1ccccc1] |
| 7 | 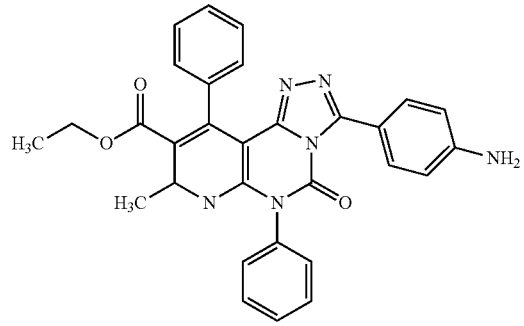 [SMILES: CCOC(=O)C1=C(c2ccccc2)c2c(n(-c3ccccc3)c(=O)n3c(-c4ccc(N)cc4)nnc23)NC1C] |
| 8 | 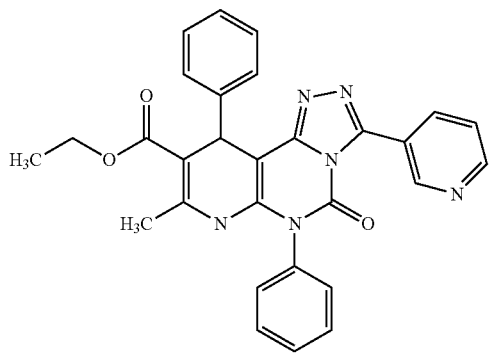 [SMILES: CCOC(=O)C1=C(C)Nc2c(c3nnc(-c4cccnc4)n3c(=O)n2-c2ccccc2)C1c1ccccc1] |
| 9 | 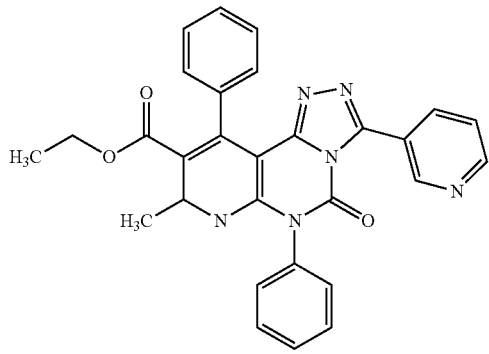 [SMILES: CCOC(=O)C1=C(c2ccccc2)c2c(n(-c3ccccc3)c(=O)n3c(-c4cccnc4)nnc23)NC1C] |
| 10 | 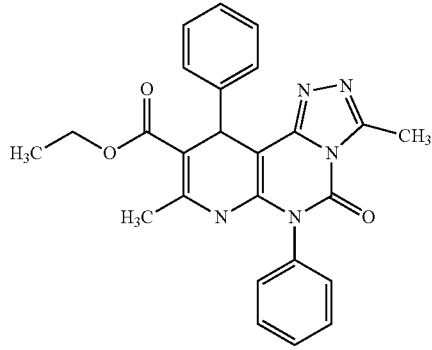 [SMILES: CCOC(=O)C1=C(C)Nc2c(c3nnc(C)n3c(=O)n2-c2ccccc2)C1c1ccccc1] |
| 11 | 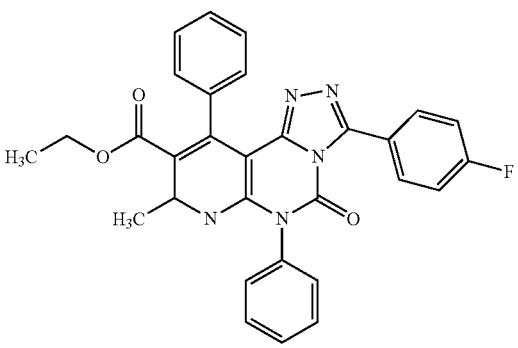 [SMILES: CCOC(=O)C1=C(c2ccccc2)c2c(n(-c3ccccc3)c(=O)n3c(-c4ccc(F)cc4)nnc23)NC1C] |
| 12 | 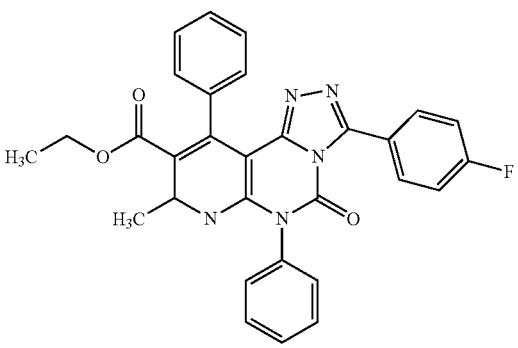 [SMILES: CCOC(=O)C1=C(c2ccccc2)c2c(n(-c3ccccc3)c(=O)n3c(-c4ccc(F)cc4)nnc23)NC1C] |
| 13 | 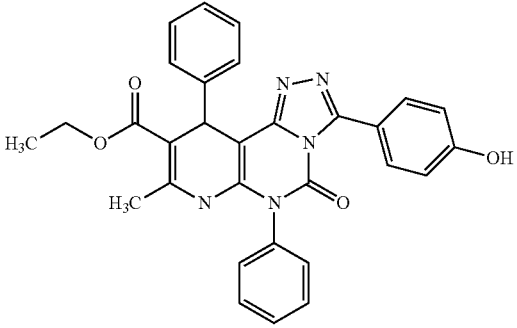 [SMILES: CCOC(=O)C1=C(C)Nc2c(c3nnc(-c4ccc(O)cc4)n3c(=O)n2-c2ccccc2)C1c1ccccc1] |

TABLE 1-continued

| Example | Structure |
|---------|-----------|
| 14 | 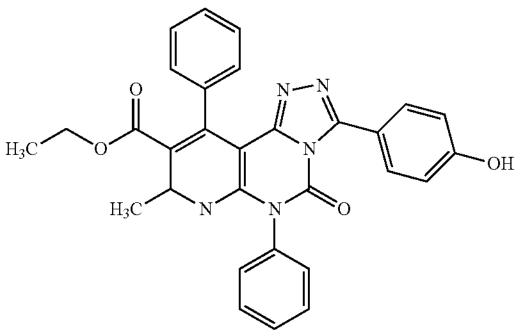 [SMILES: CCOC(=O)C1=C(c2ccccc2)c2c(n(-c3ccccc3)c(=O)n3c(-c4ccc(O)cc4)nnc23)NC1C] |
| 15 | 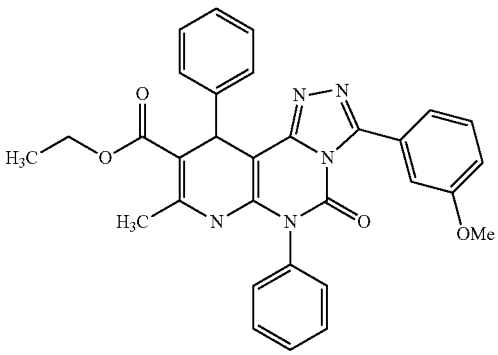 [SMILES: CCOC(=O)C1=C(C)Nc2c(c3nnc(-c4cccc(OC)c4)n3c(=O)n2-c2ccccc2)C1c1ccccc1] |
| 16 | 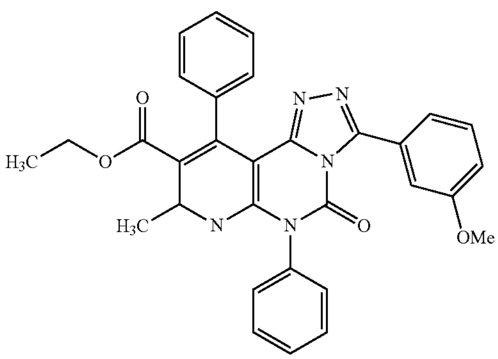 [SMILES: CCOC(=O)C1=C(c2ccccc2)c2c(n(-c3ccccc3)c(=O)n3c(-c4cccc(OC)c4)nnc23)NC1C] |
| 17 | 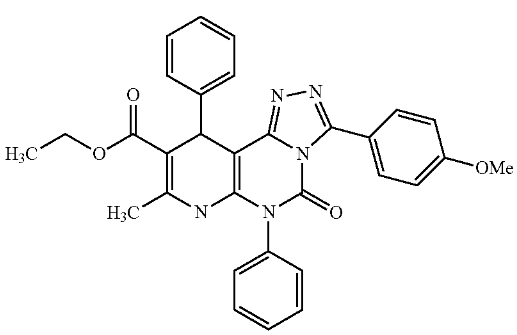 [SMILES: CCOC(=O)C1=C(C)Nc2c(c3nnc(-c4ccc(OC)cc4)n3c(=O)n2-c2ccccc2)C1c1ccccc1] |
| 18 | |
| 19 | |
| 20 | |
| 21 | |

TABLE 1-continued
| Example | Structure |
|---|---|
| 22 | 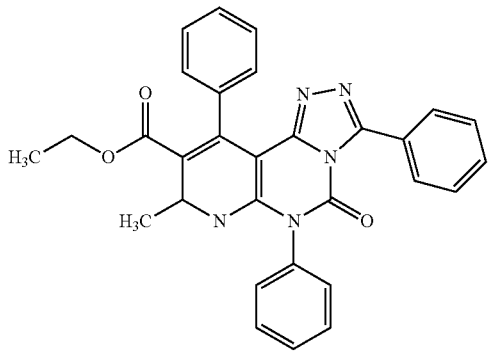 [SMILES: CCOC(=O)C1=C(c2ccccc2)c2c(n(-c3ccccc3)c(=O)n3c(-c4ccccc4)nnc23)NC1C] |
| 23 | 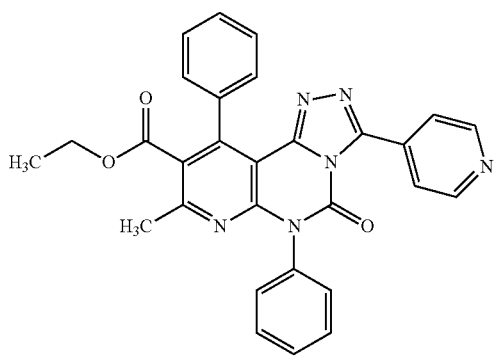 [SMILES: CCOC(=O)c1c(C)nc2c(c1-c1ccccc1)c1nnc(-c3ccncc3)n1c(=O)n2-c1ccccc1] |
| 24 | 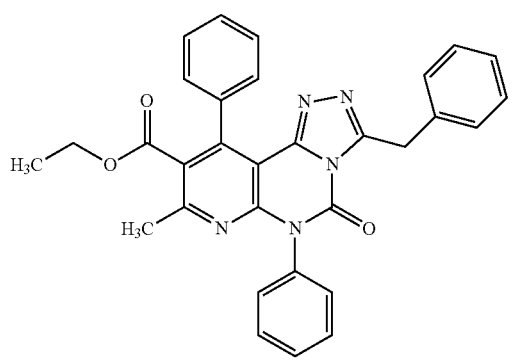 [SMILES: CCOC(=O)c1c(C)nc2c(c1-c1ccccc1)c1nnc(Cc3ccccc3)n1c(=O)n2-c1ccccc1] |
| 25 | 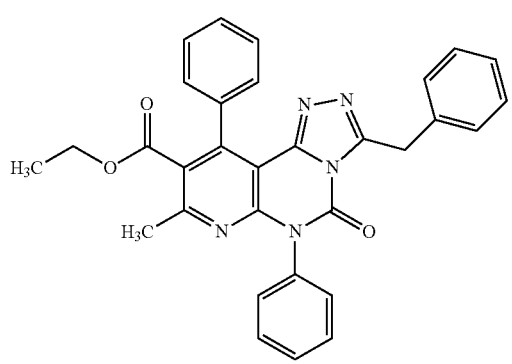 [SMILES: CCOC(=O)c1c(C)nc2c(c1-c1ccccc1)c1nnc(Cc3ccccc3)n1c(=O)n2-c1ccccc1] |
| 26 | 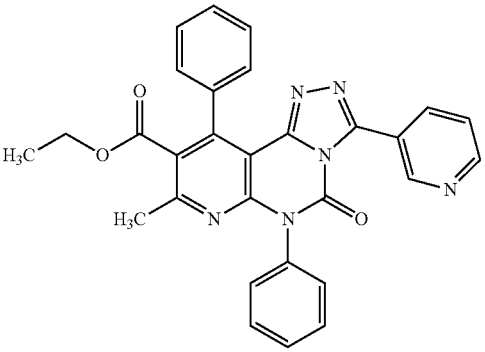 [SMILES: CCOC(=O)c1c(C)nc2c(c1-c1ccccc1)c1nnc(-c3cccnc3)n1c(=O)n2-c1ccccc1] |
| 27 | 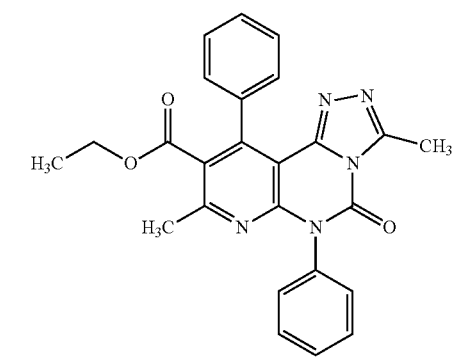 [SMILES: CCOC(=O)c1c(C)nc2c(c1-c1ccccc1)c1nnc(C)n1c(=O)n2-c1ccccc1] |
| 28 | 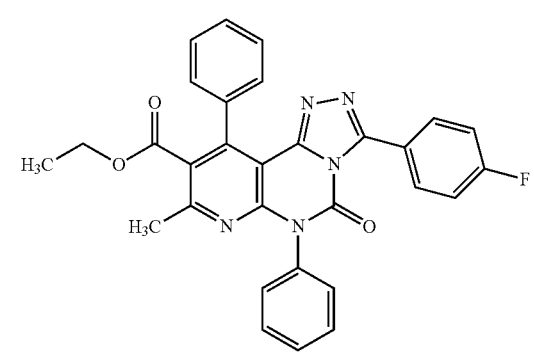 [SMILES: CCOC(=O)c1c(C)nc2c(c1-c1ccccc1)c1nnc(-c3ccc(F)cc3)n1c(=O)n2-c1ccccc1] |
| 29 | 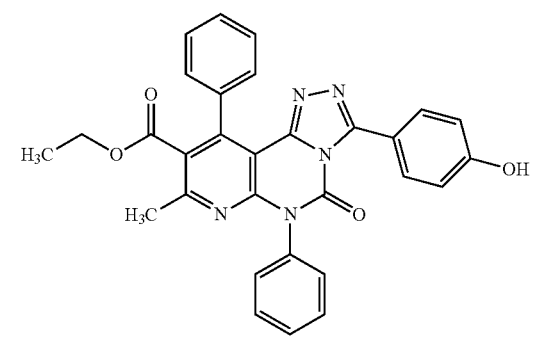 [SMILES: CCOC(=O)c1c(C)nc2c(c1-c1ccccc1)c1nnc(-c3ccc(O)cc3)n1c(=O)n2-c1ccccc1] |

TABLE 1-continued

| Example | Structure |
|---|---|
| 30 | 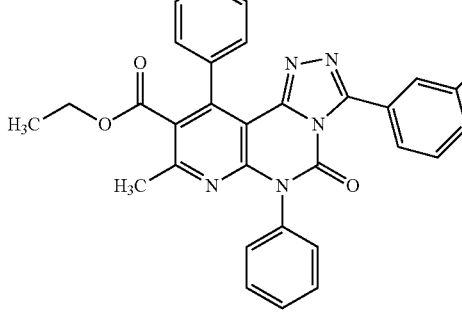 |
| 31 | 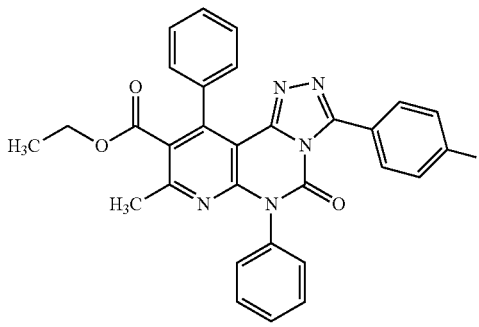 |
| 32 | 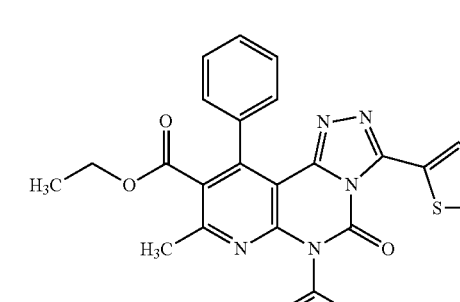 |
| 33 | 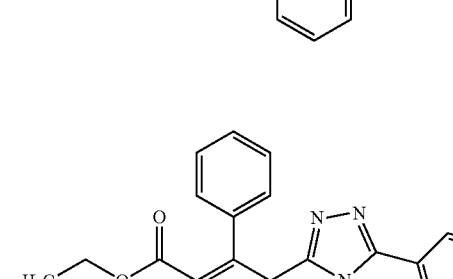 |
| 34 |  |

Example 35

Examination of Wnt Signalling Pathway Inhibiting Activity of Compounds (15), (16) and (18)

To screen for small-molecule modulators of the Wnt signalling pathway, a reporter gene based assay describing the modulation of the TCF4 transcription factor was used. More specifically 4000 Hek293T cells were seeded into 384 high density plates. 24 h after seeding a Wnt-sensitive reporter (6×TCF-luciferase (Firefly) (pTOP-FLASH; "Armadillo co activates transcription driven by the product of the drosophila segment polarity gene dTCF", Cell, 1997, 88(6), pages 789-799) and constitutively expressed control reporter (Renilla luciferase pCMV-RL) were transfected into Hek293T. Wnt signaling was stimulated by cotransfecting mouse Wnt1, mouse Frizzled 8 and human LRP6 according to "Casein kinase 1 gamma couples Wnt receptor activation to cytoplasmic signal transduction", Nature, 2005, 438 (7069), pages 867-872. 24 h after pathway stimulation compounds were added at a concentration of 10 microM and allowed to incubate for 24 h. For the evaluation of the $IC_{50}$ the compound was applied in increasing concentrations yielding final concentrations per well of 5 nM-100 microM.

The Wnt inhibiting activity profile of compounds (15), (16) and (18) is shown in table 2.

The $IC_{50}$ of the Wnt signalling pathway inhibiting activity of compounds (15), (16) and (18) is estimated to be 1.34+/−1.03, 2.94+/−1.03, 22.13+/−1.6 microM, respectively.

TABLE 2

Wnt inhibiting activity profile and antiproliferative activity of compounds (15), (16) and (18)

| Concentration in microM | Normalized Wnt pathway (inhibitory) activity of (15) | Normalized Wnt pathway (inhibitory) activity of (16) | Normalized Wnt pathway (inhibitory) activity of (18) |
|---|---|---|---|
| 100.000 | 0.4505 | 0.1990 | 0.2505 |
| 33.333 | 0.4200 | 0.3063 | 0.4930 |
| 11.111 | 0.2350 | 0.3755 | 0.6365 |
| 3.704 | 0.2973 | 0.5445 | 0.8798 |
| 1.235 | 0.8830 | 0.9565 | 0.7260 |
| 0.412 | 0.9830 | 1.0435 | 1.1223 |
| 0.137 | 1.0963 | 1.0070 | 1.0825 |
| 0.046 | — | 1.0533 | 1.0168 |

TABLE 2-continued

Wnt inhibiting activity profile and antiproliferative
activity of compounds (15), (16) and (18)

| Concen-tration in microM | Normalized Wnt pathway (inhibitory) activity of (15) | Normalized Wnt pathway (inhibitory) activity of (16) | Normalized Wnt pathway (inhibitory) activity of (18) |
|---|---|---|---|
| 0.015 | 0.9230 | 1.2275 | 1.1175 |
| 0.005 | 0.9417 | 0.9907 | 0.8680 |

Example 36

Examination of Toxicity in Hek293T and HepG2

For examination of cytotoxicity in these cancer cell lines the commercial available CellTiterGlo® Reagent (Promega, USA) was used according to the manufactor. Compounds were applied to Hek293T (denoted (1)) or HepG2 (denoted (2)), cultured in Dulbecco's Modified Eagles Medium, supplemented with 10% fetal calf serum and 1% penicillin/streptomycin. Cells were grown in T75 flasks at 37° C., 5% CO2 and trypsinized when 60-80% confluent by adding 2 ml of 0.25% Trypsin-EDTA solution. Cells were then re-suspended into culture medium yielding approx. 4000 cells (1) or 4500 cells (2), suspended in 30 microl medium. 48 h after cell seeding, compounds were added to yield the desired final concentrations. 24 h after compound addition cytotoxicity was evaluated. For this purpose the media was removed and CellTiterGlo® was added according to the manufactors manual. In this assay the luciferase emission readout is directly correlated with the cellular amount of ATP, low luciferase emission thus is reflecting cytotoxicity of a compound. For the evaluation of the $IC_{50}$ the compound was applied in increasing concentrations yielding final concentrations per well of 5 nM-100 microM.

The cytotoxic activity profile of the denoted compounds in Hek293T and HepG2 is shown in table 3 and 4.

Toxicity was not observed in Hek293T or HepG2 even at the highest concentration (100 microM) used in the titration experiment.

TABLE 3

Toxicity profile on Hek293T of compounds
(15), (16) and (18):

| Concen-tration in microM | Normalized toxicity values (Hek293T) of (15) | Normalized toxicity values (Hek293T) of (16) | Normalized toxicity values (Hek293T) of (18) |
|---|---|---|---|
| 100.000 | 1.4175 | 0.9233 | 0.9883 |
| 33.333 | 1.0515 | 0.9450 | 1.1175 |
| 11.111 | 1.1550 | 0.9213 | 1.0825 |
| 3.704 | 1.0113 | 0.8778 | 1.1200 |
| 1.235 | 0.8915 | 0.8530 | 1.0733 |
| 0.412 | 0.9603 | 0.8593 | 1.0313 |
| 0.137 | 0.9283 | 0.8375 | 1.0088 |
| 0.046 | 1.2200 | 0.8370 | 1.0523 |
| 0.015 | 1.0500 | 0.8660 | 1.0110 |
| 0.005 | 1.1205 | 1.0215 | 1.1075 |

TABLE 4

Toxicity Profile on HepG2 of compounds (15),
(16) and (18):

| Concen-tration in microM | Normalized toxicity values (HepG2) of (15) | Normalized toxicity values (HepG2) of (16) | Normalized toxicity values (HepG2) of (18) |
|---|---|---|---|
| 100.000 | 1.5075 | 1.1200 | 1.1375 |
| 33.333 | 1.2000 | 1.2425 | 1.1125 |
| 11.111 | 1.1825 | 1.1325 | 1.0800 |
| 3.704 | 1.1575 | 1.0303 | 0.9855 |
| 1.235 | 0.9878 | 0.9173 | 0.9953 |
| 0.412 | 1.0390 | 0.9183 | 0.9185 |
| 0.137 | 0.9913 | 0.9210 | 0.9173 |
| 0.046 | 1.1350 | 0.9210 | 1.0350 |
| 0.015 | 1.0465 | 0.9130 | 1.0110 |
| 0.005 | 1.0700 | 1.0275 | 1.1400 |

Example 37

Examination of Cell Line Specific Cytotoxicity

For examination of cell line-specific cytotoxicity, compounds were applied to human colorectal cancer cells (HCT116, denoted (1); SW480, denoted (2); Dld-1, denoted (3)) and human fibroblasts (HFF-1, denoted (4); HS-68, denoted (5)), cultured in Mc Coy's (1) and Dulbecco's Modified Eagles Medium (2-5), supplemented with 10% ((1)-(3)) and 20% ((4), (5)) fetal calf serum and 1% penicillin/streptomycin. Cells were grown in T75 flasks at 37° C., 5% CO2 and trypsinized when 60-80% confluent by adding 2 ml of 0.25% Trypsin-EDTA solution. Cells were then re-suspended into culture medium and approx. 750 cells, suspended in 45 microl medium, were plated into each well of a black 384-well plate for fluorescence imaging experiments. 24-36 hr later 5 microl compound solution (100 microM compound dissolved in ultra pure water containing 1% DMSO), were added to achieve a final concentration of 10 microM and were incubated for at least 72 hr. Compound incubation was terminated by (a) fixation and (b) permeabilisation of cells, followed by (c) fluorescence labeling of cell nuclei for cytometric quantification or by immunocytochemistry for microscopic evaluation of cell morphology. The three steps were performed by replacing the solution of the previous step in each well of a 384-well plate by (a) 30 microl PBS (phosphate buffered saline) containing 5% PFA (paraformaldehyde), (b) 30 microl PBS containing 0.2% TritonX-100 and (c) 10 microl PBS containing Hoechst-33342 for cytometry or Hoechst-33342, FITC (fluorescein isothiocyanate-) labeled α-tubulin antibodies and TRITC-(tetramethylrhodamine isothiocyanate-) labeled phalloidin antibodies for microscopy. Solutions were incubated for 15 (a,b) and 30 min (c) in the dark at room temperature. Cells were washed twice between each step with 30 microl PBS. The assay system was miniaturized and adapted to automated workflow using liquid-handling robotics.

Cell line-specific cytotoxicity was quantified by counting the number of Hoechst labeled nuclei per well of a 384-well plate using a plate cytometer. Data obtained with the cytometer was analysed using standard data analysis software.

Identified hits were further evaluated by visual inspection of fluorescence micrographs obtained from imaging using a conventional fluorescence microscope.

The results are shown in Table 5.

TABLE 5

Influence of compounds (15), (16) and (18) on normal cells (HS68):

| Concentration in micoM | Normalized cell count (HS68) of 15 | Normalized cell count (HS68) of 16 | Normalized cell count (HS68) of 18 |
|---|---|---|---|
| 100.000 | 0.90986 | 0.90459 | 0.4385 |
| 33.333 | 0.95925 | 0.80046 | 0.36512 |
| 11.111 | 0.97565 | 1.14365 | 0.54989 |
| 3.704 | 0.97721 | 1.17515 | 0.79518 |
| 1.235 | 0.96097 | 1.05091 | 1.01408 |
| 0.412 | 0.94837 | 1.11125 | 0.97361 |
| 0.137 | 0.99672 | 1.05643 | 0.94879 |
| 0.046 | 1.01796 | 1.03845 | 1.01355 |
| 0.015 | 0.91659 | 0.99039 | 0.99384 |
| 0.005 | 1 | 1 | 1 |

Example 38

Examination of the Antiproliferative Activity of Compounds (15), (16) and (18) Against Human Colon Carcinoma Cells HCT116

The examination of the antiproliferative activity against human colon carcinoma cells HCT116 was carried out in analogy to example 35. The compounds are applied in increasing concentrations yielding final concentrations per well of 30 nM-100 microM. Compounds of the present invention have potent antiproliferative activity against human colon carcinoma cells as shown for HCT116 in Table 6.

TABLE 6

Influence of compounds (15), (16) and (18) on HCT116 colon carcinoma alls:

| Concentration in microM | Normalized cell count (HCT 116) of 15 | Normalized cell count (HCT 116) of 16 | Normalized cell count (HCT 116) of 18 |
|---|---|---|---|
| 100.000 | 0.14963 | 0.58013 | 0.18917 |
| 33.333 | 0.25699 | 0.51996 | 0.15553 |
| 11.111 | 0.27161 | 1.23078 | 0.15954 |
| 3.704 | 0.72348 | 1.19973 | 0.41544 |
| 1.235 | 0.86499 | 1.12537 | 0.83991 |
| 0.412 | 0.92188 | 1.06742 | 0.91656 |
| 0.137 | 0.93127 | 1.05958 | 0.86029 |
| 0.046 | 1.01291 | 1.16277 | 0.98585 |
| 0.015 | 1.03895 | 1.06254 | 0.93772 |
| 0.005 | 1 | 1 | 1 |

The invention claimed is:
1. A compound having the formula:

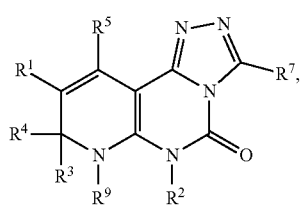

(Ia)

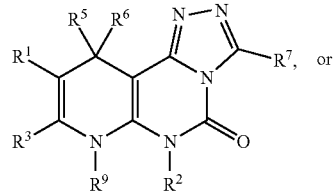

(Ib)

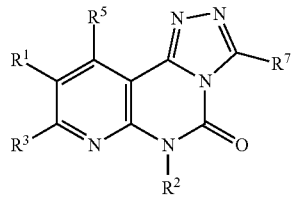

(Ic)

wherein:
(a) $R^1$ is:
(i) selected from the group consisting of OH, $OR^{15}$, COOH, $COOR^{15}$, CHO, $CONR^{15}R^{16}$, $C=N-OR^{15}$, $C=N-NR^{15}R^{16}$, $C=N-NR^{15}-COR^{16}$, $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl, wherein the alkyl, alkoxy, acyl, alkenyl, alkinyl, cycloalkyl, cycloalkenyl, aryl, aryloxy and aralkyl (1) optionally comprises 1 to 4 heteroatoms selected from the group consisting of N, O and S and/or one or more CO functional groups in the chain or cycle, and (2) is optionally substituted by one or more substituents selected, independently from each other, from the group consisting of $C_1$-$C_8$ alkyl, $C_1$-$C_8$ alkoxy, $C_1$-$C_8$ acyl, $C_1$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy, $C_4$-$C_{15}$ aralkyl, F, Cl, Br, I, CN, CHO, OH, $OR^{12}$, $SR^{12}$, $NR^{12}R^{13}$, COOH, $COOR^{12}$, $CONR^{12}R^{13}$, $SO_2R^{12}$, $SO_2NR^{12}R^{13}$, $SONR^{12}R^{13}$, $NR^{12}SOR^{13}$, $NR^{12}SO_2R^{13}$, $NR^{12}SO_2NR^{13}R^{14}$, $NR^{12}COR^{13}$, $NR^{12}CONR^{13}$, $NR^{12}COOR^{13}$, $OCONR^{12}R^{13}$, wherein the alkyl, alkoxy, acyl, alkenyl, alkinyl, cycloalkyl, cycloalkenyl, aryl, aryloxy and aralkyl optionally comprises 1 to 4 heteroatoms selected from the group consisting of N, O and S and/or one or more CO functional groups in the chain or cycle; or
(ii) $R^1$ forms together with $R^3$ a 5 to 7 membered saturated or unsaturated ring having a lactam, lacton, diimid or anhydride or 1 to 2 ether bondings, wherein the 5 to 7 membered ring is optionally substituted by one or more substituents selected, independently from each other, from the group consisting of F, Cl, Br, I, CN, CHO, OH, $OR^{12}$, $SR^{12}$, $NR^{12}R^{13}$, COOH, $COOR^{12}$, $CONR^{12}R^{13}$, $SO_2R^{12}$, $SO_2NR^{12}R^{13}$, $SONR^{12}R^{13}$, $NR^{12}SOR^{13}$, $NR^{12}SO_2R^{13}$, $NR^{12}SO_2NR^{13}R^{14}$, $NR^{12}COR^{13}$, $NR^{12}CONR^{13}R^{14}$, $NR^{12}COOR^{13}$, $OCONR^{12}R^{13}$, $C_1$-$C_8$ alkyl, $C_1$-$C_8$ alkoxy, $C_1$-$C_8$ acyl, $C_2$-$C_8$ alkenyl, $C_3$-$C_8$ cycloalkyl, $C_3$-$C_8$ cycloalkenyl, $C_3$-$C_7$ aryl, $C_4$-$C_{13}$ aralkyl and $C_3$-$C_7$ aryloxy, wherein the alkyl, alkoxy, acyl, alkenyl, alkinyl, cycloalkyl, cycloalkenyl, aryl, aralkyl and aryloxy (1) optionally comprises 1 to 4 heteroatoms selected from the group consisting of N, O and S and/or one or more CO functional groups in the chain or cycle and (2) is optionally substituted by one or more substituents selected, independently from each other, from the group consisting of $C_1$-$C_8$ alkyl, $C_1$-$C_8$ alkoxy, $C_1$-$C_8$ acyl, $C_1$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy, $C_4$-$C_{15}$ aralkyl, F, Cl, Br, I, CN, CHO, OH, $OR^{12}$, $SR^{12}$, $NR^{12}R^{13}$, COOH, $COOR^{12}$, $CONR^{12}R^{13}$, $SO_2R^{12}$, $SO_2NR^{12}R^{13}$, $SONR^{12}R^{13}$, $NR^{12}SOR^{13}$, $NR^{12}SO_2R^{13}NR^{12}SONR^{13}R^{14}$, $NR^{12}COR^{13}$, $NR^{12}CONR^{13}R^{14}$, $NR^{12}COOR^{13}$, $OCONR^{12}R^{13}$, wherein the alkyl, alkenyl, alkoxy, acyl, alkenyl, alkinyl, cycloalkyl, cycloalkenyl, aryl, aryloxy and aralkyl optionally comprises 1 to 4 heteroatoms selected from the group consisting of N, O and S and/or one or more CO functional groups in the chain or cycle;

(b) $R^2$ and $R^9$ are each independently selected from the group consisting of H, $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl, wherein the alkyl, alkoxy, acyl, alkenyl, alkinyl, cycloalkyl, cycloalkenyl, aryl, aryloxy and aralkyl optionally (1) comprises 1 to 4 heteroatoms selected from the group consisting of N, O and S and/or one or more CO functional groups in the chain or cycle and (2) is optionally substituted by one or more substituents selected, independently from each other, from the group consisting of $C_1$-$C_8$ alkyl, $C_1$-$C_8$ alkoxy, $C_1$-$C_8$ acyl, $C_2$-$C_8$ alkenyl, $C_2$-$C_8$ alkinyl, $C_3$-$C_8$ cycloalkyl, $C_3$-$C_8$ cycloalkenyl, $C_3$-$C_7$ aryl, $C_3$-$C_7$ aryloxy, $C_4$-$C_{15}$ aralkyl, F, Cl, Br, I, CN, CHO, OH, $OR^{12}$, $SR^{12}$, $NR^{12}R^{13}$, COOH, $COOR^{12}$, $CONR^{12}R^{13}$, $SO_2R^{12}$, $SO_2NR^{12}R^{13}$, $SONR^{12}R^{13}$, $NR^{12}SOR^{13}$, $NR^{12}SO_2R^{13}$, $NR^{12}SO_2NR^{13}R^{14}$, $NR^{12}COR^{13}$, $NR^{12}CONR^{13}R^{14}$, $NR^{12}COOR^{13}$, and $OCONR^{12}R^{13}$, wherein the alkyl, alkoxy, acyl, alkenyl, alkinyl, cycloalkyl, cycloalkenyl, aryl, aryloxy and aralkyl optionally comprises 1 to 4 heteroatoms selected from the group consisting of N, O and S and/or one or more CO functional groups in the chain or cycle;

(c) $R^3$ and $R^4$ are
 (i) selected, independently from each other, from the group consisting of H, $C_1$-$C_8$ alkyl, $C_1$-$C_6$ alkenyl, $C_3$-$C_7$ cycloalkyl and $C_3$-$C_7$ aryl, wherein the alkyl, alkenyl, cyloalkyl and aryl (1) optionally comprises 1 to 4 hetero atoms selected from the group consisting of N, O and S and/or one of more CO functional groups and (2) is optionally substituted by one or more substituents selected from the group consisting of F, Cl, Br, I, CN, CHO, OH, $OR^{12}$, $SR^{12}$, $NR^{12}R^{13}$, COOH, $COOR^{12}$, $CONR^{12}R^{13}$, $SO_2R^{12}$, $SO_2NR^{12}R^{13}$, $SONR^{12}R^{13}$, $NR^{12}SOR^{13}$, $NR^{12}SO_2R^{13}NR^{12}SO_2NR^{13}R^{14}$, $NR^{12}COR^{13}$, $NR^{12}CONR^{13}R^{14}$, $NR^{12}COOR^{13}$, $OCONR^{12}R^{13}$; or
 (ii) $R^3$ forms together with $R^1$ a 5 to 7 membered saturated or unsaturated ring having a lactam, lacton, diimid or anhydride or 1 to 2 ether bondings, wherein the 5 to 7 membered ring is optionally substituted by one or more substituents selected, independently from each other, from the group consisting of F, Cl, Br, I, CN, CHO, OH, $OR^{12}$, $SR^{12}$, $NR^{12}R^{13}$, COOH, $COOR^{12}$, $CONR^{12}R^{13}$, $SO_2R^{12}$, $SO_2NR^{12}R^{13}$, $SONR^{12}R^{13}NR^{12}SOR^{13}NR^{12}SOR^{13}NR^{12}SONR^{13}R^{14}$, $NR^{12}COR^{13}$, $NR^{12}CONR^{13}R^{14}$, $NR^{12}COOR^{13}$, $OCONR^{12}R^{13}$, $C_1$-$C_8$ alkyl, $C_1$-$C_8$ alkoxy, $C_1$-$C_8$ acyl, $C_7$-$C_8$ alkenyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl, wherein the alkyl, alkoxy, acyl, alkenyl, cycloalkyl, cycloalkenyl, aryl, aryloxy and aralkyl (1) optionally comprises 1 to 4 heteroatoms selected from the group consisting of N, O and S and/or one of more CO functional groups in the chain or cycle and (2) is optionally substituted by one or more substituents selected, independently from each other, from the group consisting of $C_1$-$C_8$ alkyl, $C_1$-$C_8$ alkoxy, $C_1$-$C_8$ acyl, $C_7$-$C_8$ alkenyl, $C_3$-$C_8$ cycloalkyl, $C_3$-$C_8$ cycloalkenyl, $C_3$-$C_7$ aryl, aryloxy, F, Cl, Br, I, CN, CHO, OH, $OR^{12}$, $SR^{12}$, $NR^{12}R^{13}$, COOH, $COOR^{12}$, $CONR^{12}R^{13}$, $SO_2R^{12}$, $SO_2NR^{12}R^{13}$, $SONR^{12}R^{13}$, $NR^{12}SOR^{13}$, $NR^{12}SO_2R^{13}NR^{12}SO_2NR^{13}R^{14}$, $NR^{12}COR^{13}$, $NR^{12}CONR^{13}R^{14}$, $NR^{12}COOR^{13}$, and $OCONR^{12}R^{13}$, wherein the alkyl, alkoxy, acyl, alkenyl, cycloalkyl, cycloalkenyl, aryl and aryloxy optionally comprises 1 to 4 heteroatoms selected from the group consisting of N, O and S and/or one of more CO functional groups in the chain or cycle;

(d) $R^5$ and $R^6$ are selected independently from each other from the group as defined for $R^3$ and $R^4$ with the proviso that neither $R^5$ nor $R^6$ form a 5- to 7-membered ring with $R^1$;

(e) $R^7$ is selected from the group consisting of H, $C_1$-$C_8$ alkyl, $C_7$-$C_8$ alkenyl, $C_3$-$C_8$ cycloalkyl, $C_3$-$C_8$ cycloalkenyl, $C_3$-$C_7$ aryl, $C_3$-$C_7$ aryloxy and $C_4$-$C_{15}$ aralkyl, wherein the alkyl, alkenyl, cycloalkyl, cycloalkenyl, aryl, aryloxy and aralkyl (1) optionally comprises 1 to 4 heteroatoms selected from the group consisting of N, O and S and/or one of more CO functional groups in the chain or cycle and (2) is optionally substituted by one or more substituents selected, independently from each other, from the group consisting of $C_1$-$C_8$ alkyl, $C_1$-$C_8$ alkoxy, $C_1$-$C_8$ acyl, $C_2$-$C_8$ alkenyl, $C_3$-$C_8$ cycloalkyl, $C_3$-$C_8$ cycloalkenyl, $C_3$-$C_7$ aryl, $C_3$-$C_7$ aryloxy, $C_4$-$C_{15}$ aralkyl, F, Cl, Br, I, CN, CHO, OH, $OR^{12}$, $SR^{12}$, $NR^{12}R^{13}$, COOH, $COOR^{12}$, $CONR^{12}R^{13}SO_2R^{12}$, $SO NR^{12}R^{13}$, $SONR^{12}R^{13}$, $NR^{12}SOR^{13}$, $NR^{12}SO_7R^{13}NR^{12}SO_7NR^{13}R^{14}$, $NR^{12}COR^{13}$, $NR^{12}CONR^{13}R^{14}$, $NR^{12}COOR^{13}$, and $OCONR^{12}R^{13}$, wherein the substituents alkyl, alkoxy, acyl, alkenyl, alkinyl, cycloalkyl, cycloalkenyl, aryl, aryloxy and aralkyl optionally comprises 1 to 4 heteroatoms selected from the group consisting of N, O and S and/or one of more CO functional groups in the chain or cycle, wherein the substituents alkyl, alkoxy, acyl, alkenyl, cycloalkyl, cycloalkenyl, aryl, aryloxy and aralkyl is optionally substituted by one or more substituents selected from the group consisting of OH, F, Cl, Br, I, CN, $C_1$-$C_4$ alkyl, $C_7$-$C_4$ alkenyl, $C_1$-$C_4$ alkoxy, $C_5$-$C_7$ aryl, $C_3$-$C_8$ cycloalkyl and $C_5$-$C_7$ aryloxy;

(f) $R^{12}$, $R^{13}$, $R^{14}$, $R^{15}$ and $R^{16}$ are selected, independently from each other, from the group consisting of H, OH, $C_1$-$C_8$ alkyl, $C_1$-$C_8$ alkoxy, $C_1$-$C_8$ acyl, $C_2$-$C_8$ alkenyl, alkinyl, $C_3$-$C_8$ cycloalkyl, $C_3$-$C_8$ cycloalkenyl, $C_3$-$C_7$ aryl, $C_3$-$C_7$ aryloxy and $C_4$-$C_{13}$ aralkyl, optionally comprising 1 to 4 heteroatoms selected from the group consisting of N, O and S and/or one of more CO functional groups in the chain or cycle, wherein the alkyl, alkoxy, acyl, alkenyl, alkinyl, cycloalkyl, cycloalkenyl, aryl, araloxy and aralkyl is optionally substituted by one or more substituents selected from the group consisting of OH, F, Cl, Br, I, CN, $C_1$-$C_4$ alkyl, $C_1$-$C_4$ alkenyl, alkoxy, $C_5$-$C_7$ aryl, $C_3$-$C_8$ cycloalkyl and $C_5$-$C_7$ aryloxy, wherein alkyl, alkenyl, alkoxy, acyl, alkenyl, alkinyl and aralkyl is linear or branched;

or a solvate, hydrate, ester, or pharmaceutically acceptable salt thereof.

2. A compound having the formula

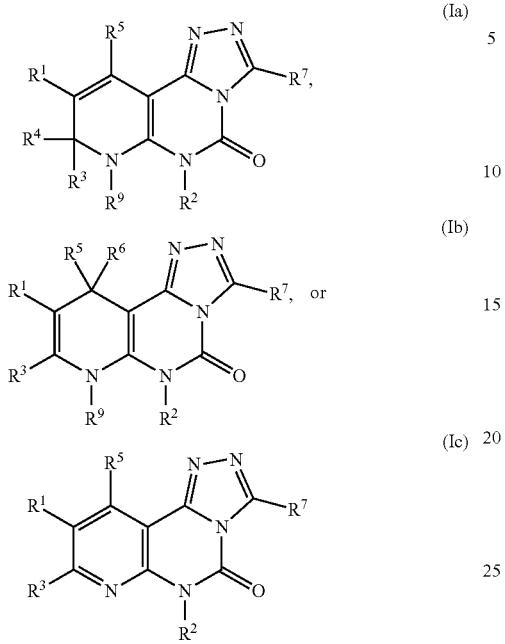

wherein:
(a) $R^1$ is:
  (i) selected from the group consisting of OH, $OR^{15}$, COOH, $COOR^{15}$, CHO, $CONR^{15}R^{16}$, $C=N-OR^{15}$, $C=N-NR^{15}-COR^{16}$, $C_1$-$C_8$ alkyl, $C_2$-$C_8$ alkenyl, $C_3$-$C_8$ cycloalkyl, $C_3$-$C_7$ aryl and $C_4$-$C_{15}$ aralkyl, wherein the alkyl, alkenyl, cycloalkyl, aryl and aralkyl (1) optionally comprises 1 to 4 heteroatoms selected from the group consisting of N, O and S in the chain or cycle and (2) is optionally substituted by one or more substituents selected, independently from each other, from the group consisting of $C_1$-$C_8$ alkyl, $C_1$-$C_8$ alkoxy, $C_3$-$C_7$ aryl, $C_3$-$C_7$ aryloxy, $C_4$-$C_{15}$ aralkyl, F, Cl, Br, I, CN, OH, $OR^{12}$, $SR^{12}$, $NR^{12}R^{13}$, COOH, $COOR^{12}$, $CONR^{12}R^{13}$, $SO_2R^{12}$ and $SO_7NR^{12}R^{13}$, wherein the alkyl, alkoxy, aryl, aryloxy and aralkyl optionally comprises 1 to 4 heteroatoms selected from the group consisting of N, O and S in the chain or cycle; or
  (ii) $R^1$ forms together with R3 a 5 to 7 membered saturated or unsaturated ring having a lactam, lacton, diimid or anhydride bonding, wherein the 5 to 7 membered ring is optionally substituted by one or more substituents selected, independently from each other, from the group consisting of F, Cl, Br, I, CN, OH, $OR^{12}$, $SR^{12}$, $NR^{12}R^{13}$, COOH, $COOR^{12}$, $CONR^{12}R^{13}$, $SO_7R^{12}$, $SO_2NR^{12}R^{13}$, $C_1$-$C_8$ alkyl, $C_1$-$C_8$ alkenyl, $C_3$-$C_8$ cycloalkyl, $C_3$-$C_7$ aryl and $C_4$-$C_{15}$ aralkyl, wherein the alkyl, alkenyl, cycloalkyl, aryl and aralkyl (1) optionally comprises 1 to 4 heteroatoms selected from the group consisting of N, O and S in the chain or cycle and (2) is optionally substituted by one or more substituents selected, independently from each other, from F, Cl, Br, I, CN, OH, $OR^{12}$, $SR^{12}$, $NR^{12}R^{13}$, COOH, $COOR^{12}$, $CONR^{12}R^{13}$, $SO_7R^{12}$, and $SO_7NR^{12}R^{13}$;
(b) $R^2$ and $R^9$ are each independently selected from the group consisting of H, $C_1$-$C_8$ alkyl, $C_1$-$C_8$ alkenyl, $C_3$-$C_8$ cycloalkyl, $C_3$-$C_7$ aryl and $C_4$-$C_{15}$ aralkyl, wherein the alkyl, alkenyl, cycloalkyl, aryl and aralkyl (1) optionally comprises 1 to 4 heteroatoms selected from the group consisting of N, O and S in the chain or cycle and (2) is optionally substituted by one or more substituents selected, independently from each other, from the group consisting of $C_1$-$C_8$ alkyl, $C_1$-$C_8$ alkoxy, $C_3$-$C_8$ cycloalkyl, $C_3$-$C_7$ aryl, $C_3$-$C_7$ aryloxy, $C_4$-$C_{15}$ aralkyl, F, Cl, Br, I, CN, OH, $OR^{12}$, $SR^{12}$, $NR^{12}R^{13}$, COOH, $COOR^{12}$, $CONR^{12}R^{13}$, $SO_2R^{12}$, and $SO_7NR^{12}R^{13}$, wherein the alkyl, alkoxy, cycloalkyl, aryl, aryloxy and aralkyl optionally comprises 1 to 4 heteroatoms selected from the group consisting of N, O and S in the chain or cycle;

(c) $R^3$ and $R^4$ are:
  (i) selected, independently from each other, from the group consisting of H, $C_1$-$C_8$ alkyl, $C_1$-$C_8$ alkenyl, $C_3$-$C_7$ cycloalkyl and $C_3$-$C_7$ aryl, wherein the alkyl, alkenyl, cyloalkyl and aryl (1) optionally comprises 1 to 4 hetero atoms selected from the group consisting of N, O and S and (2) is optionally substituted by one or more substituents selected from F, Cl, Br, I, CN, OH, $OR^{12}$, $SR^{12}$, $NR^{12}R^{13}$, COOH, $COOR^{12}$, $CONR^{12}R^{13}$, $SO_2R^{12}$, and $SO_7NR^{12}R^{13}$, or
  (ii) $R^3$ forms together with $R^1$ a 5 to 7 membered saturated or unsaturated ring having a lactam, lacton, diimid or anhydride bonding, wherein the 5 to 7 membered ring is optionally substituted by one or more substituents selected, independently from each other, from the group consisting of F, Cl, Br, I, CN, OH, $OR^{12}$, $SR^{12}$, $NR^{12}R^{13}$, COOH, $COOR^{12}$, $CONR^{12}R^{13}$, $SO_2R^{12}$, $SO_2NR^{12}R^{13}$, $C_1$-$C_8$ alkyl, $C_2$-$C_8$ alkenyl, $C_3$-$C_8$ cycloalkyl and $C_3$-$C_7$ aryl, wherein the alkyl, alkenyl, cycloalkyl and aryl (1) optionally comprises 1 to 4 heteroatoms selected from the group consisting of N, O and S in the chain or cycle and (2) is optionally substituted by one or more substituents selected, independently from each other, from the group consisting of F, Cl, Br, I, CN, OH, $OR^{12}$, $SR^{12}$, $NR^{12}R^{13}$, COOH, $COOR^{12}$, $CONR^{12}R^{13}$, $SO_2R^{12}$, and $SO_2NR^{12}R^{13}$;

(d) $R^5$ and $R^6$ are selected independently from each other from the group as defined for $R^3$ and $R^4$ with the proviso that neither $R^5$ nor $R^6$ form a 5- to 7-membered ring with R1;

(e) $R^7$ is selected from the group consisting of H, $C_1$-$C_8$ alkyl, $C_2$-$C_8$ alkenyl, $C_3$-$C_8$ cycloalkyl, $C_3$-$C_7$ aryl and $C_4$-$C_{15}$ aralkyl, wherein the alkyl, alkenyl, cycloalkyl, aryl and aralkyl (1) optionally comprises 1 to 4 heteroatoms selected from N, O or S in the chain or cycle and (2) is optionally substituted by one or more substituents selected, independently from each other, from the group consisting of $C_1$-$C_8$ alkyl, $C_1$-$C_8$ alkoxy, $C_2$-$C_8$ alkenyl, $C_3$-$C_7$ aryl, $C_3$-$C_7$ aryloxy, F, Cl, Br, I, CN, OH, $OR^{12}$, $SR^{12}$, $NR^{12}R^{13}$, COOH, $COOR^{12}$, $CONR^{12}R^{13}$, $SO_2R^{12}$, and $SO_7NR^{12}R^{13}$, wherein the substituents alkyl, alkoxy, alkenyl, aryl and aryloxy optionally comprises 1 to 4 heteroatoms selected from the group consisting of N, O and S in the chain or cycle, wherein the substituents alkyl, alkoxy, alkenyl, aryl and aryloxy is optionally substituted by one or more substituents selected from the group consisting of OH, F, Cl, Br, I, $NH_2$, $C_1$-$C_4$ alkyl;

(f) $R^{12}$, $R^{13}$, $R^{15}$ and $R^{16}$ are selected, independently from each other, from the group consisting of H, OH, $C_1$-$C_8$ alkyl, $C_1$-$C_8$ alkoxy, $C_3$-$C_8$ cycloalkyl, $C_3$-$C_7$ aryl and $C_4$-$C_{15}$ aralkyl, optionally comprising 1 to 4 heteroatoms selected from the group consisting of N, O and S in the chain or cycle, wherein the alkyl, cycloalkyl, aryl and aralkyl is optionally substituted by one or more substituents selected from the group consisting of OH, F, Cl, Br, I, CN, $C_1$-$C_4$ alkyl, $C_2$-$C_4$ alkenyl, $C_1$-$C_4$ alkoxy, $C_5$-$C_7$ aryl, $C_3$-$C_8$ cycloalkyl and $C_5$-$C_7$ aryloxy;

wherein alkyl, alkenyl, alkoxy, acyl, alkenyl, alkinyl and aralkyl is linear or branched;

or a solvate, hydrate, ester, or pharmaceutically acceptable salt thereof.

3. A method for the treatment of colon cancer in a mammal comprising administering to a mammal a therapeutically effective amount of a compound according to claim 1.

4. A pharmaceutical composition comprising the compound of claim 1.

5. A process for the preparation of a compound according to claim 1, comprising the following steps:

(a) reacting a primary amine with potassium cyanate, sodium cyanate or chlorosulfonylisocyanate to obtain an urea derivative;

(b) reacting the urea derivative with cyan acetic acid to obtain the cyanacylurea derivative followed by intramolecular cyclisation to the 6-aminouracil derivative;

(c) reacting an acetoacetate derivative with an aldehyde to obtain the 2-methylene acetoacetate derivative;

(d) reacting the 6-aminouracil derivative from step (b) and the 2-methylene acetoacetate derivative from step (c) to obtain the 2,4-dioxohexahydropyrido[2,3-d]pyrimidine-6 carboxylic acid ethyl ester;

(e) chlorinating 2,4-dioxohexahydropyrido[2,3-d]pyrimidine-6 carboxylic acid ethyl ester at C-4 to obtain 4-Chloro-7-methyl-2-oxo-tetrahydro-pyrido[2,3-d]pyrimidine-6-carboxylic acid ethyl ester; and (f) nucleophilic substitution of the chlorine in 4-Chloro-7-methyl-2-oxo-tetrahydro-pyrido[2,3-d]pyrimidine-6-carboxylic acid ethyl ester with hydrazides followed by the ring closure.

6. A method for the preparation of a medicament comprising the steps of:

(a) preparing at least one compound according to claim 1; and (b) formulating a medicament comprising at least said compound.

7. The compound of claim 1, wherein the compound is represented by formula Ia 8. The compound of claim 1, wherein the compound is represented by formula Ib 9. The compound of claim 1, wherein the compound is represented by formula Ic 10. The compound of claim 1, wherein $R^1$ is $COOR^{15}$.

11. The compound of claim 10, wherein $R^1$ is $COOCH_2CH_3$.

12. The compound of claim 1, wherein $R^3$ is a $C_1$-$C_8$ alkyl optionally comprising 1-4 heteroatoms selected from the group consisting of N, O and S, and wherein $R^4$ is H.

13. The compound of claim 12, wherein $R^3$ is methyl.

14. The compound of claim 1, wherein $R^5$ is a $C_3$-$C_7$ aryl optionally comprising 1-4 heteroatoms selected from the group consisting of N, O and S, and wherein $R^6$ is H.

15. The compound of claim 14, wherein $R^5$ is phenyl.

16. The compound of claim 1, wherein $R^2$ is a $C_3$-$C_7$ aryl optionally comprising 1-4 heteroatoms selected from the group consisting of N, O and S, and wherein $R^9$ is H.

17. The compound of claim 16, wherein $R^2$ is phenyl.

18. The compound of claim 1, wherein $R^1$ is $COOR^{15}$; $R^3$ is a $C_1$-$C_8$ alkyl optionally comprising 1-4 heteroatoms selected from the group consisting of N, O and S; $R^2$ and $R^5$ are each a $C_3$-$C_7$ aryl optionally comprising 1-4 heteroatoms selected from the group consisting of N, O and S; and $R^4$, $R^6$ and $R^9$ are each H.

19. The compound of claim 18, wherein the compound is selected from the group consisting of:

2
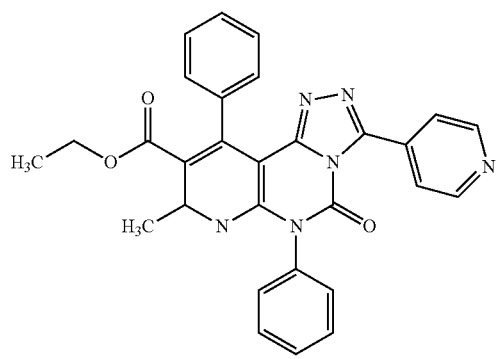
3
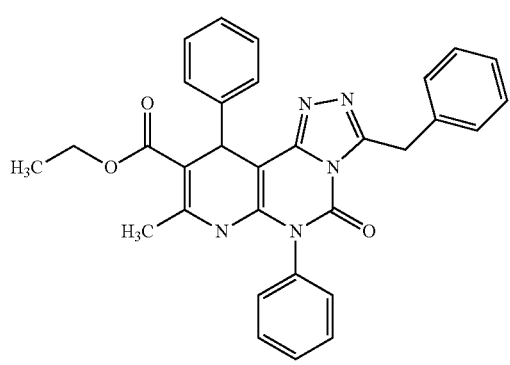
4
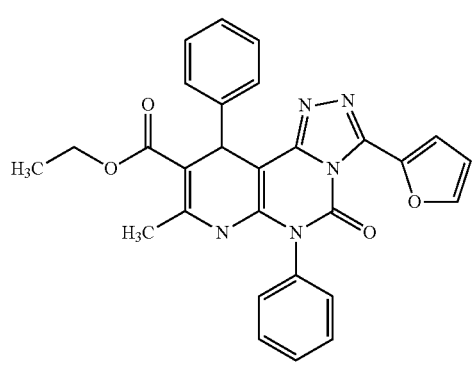
5
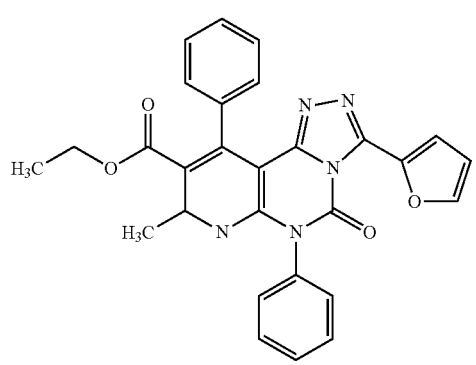
6
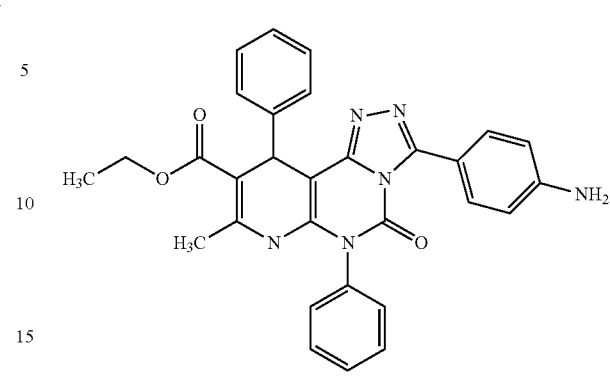
7
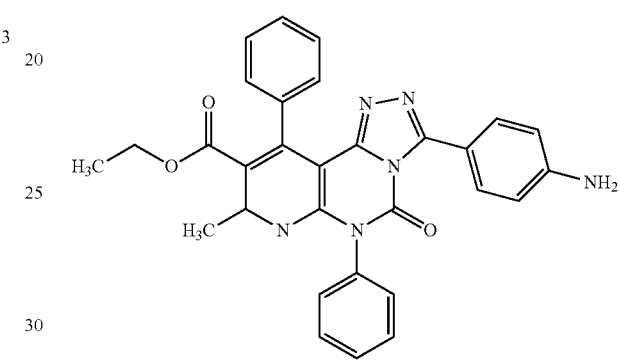
8
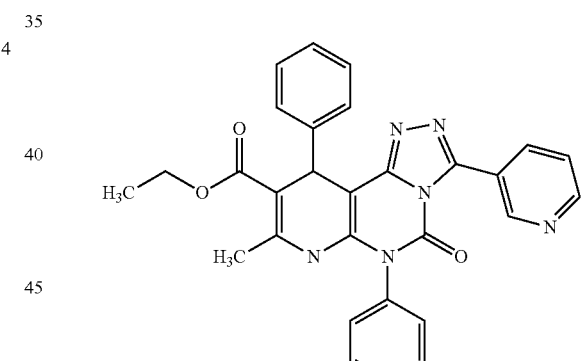
9
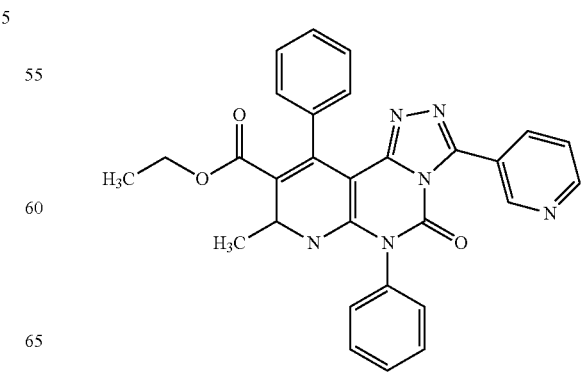

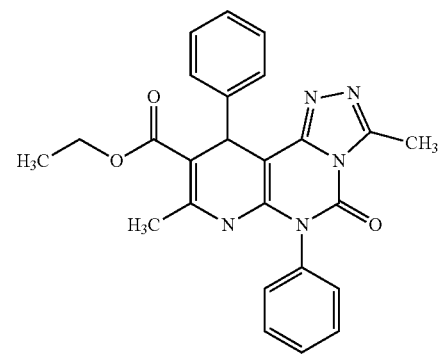
10
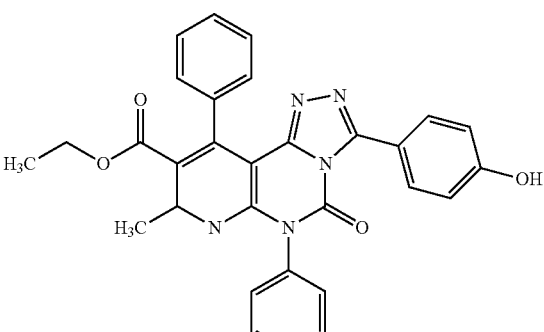
14
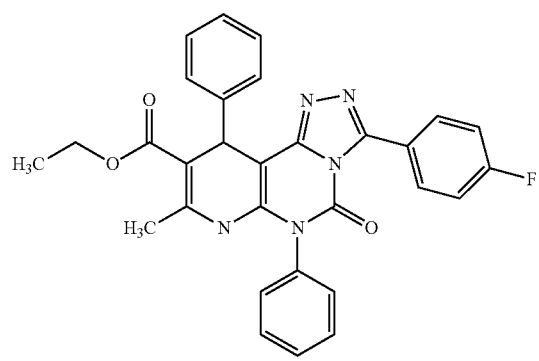
11
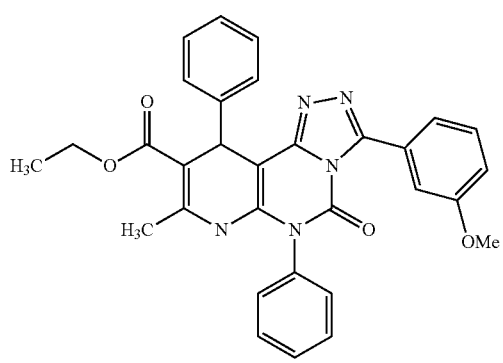
15
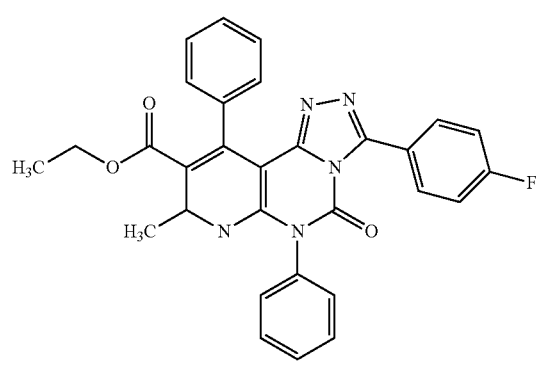
12
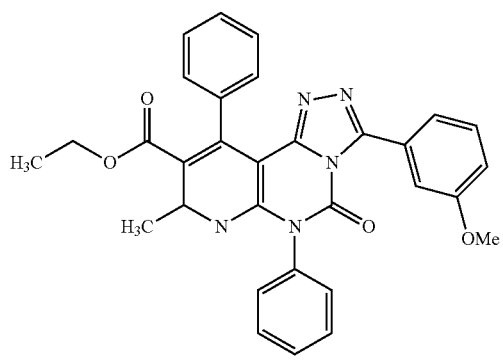
16
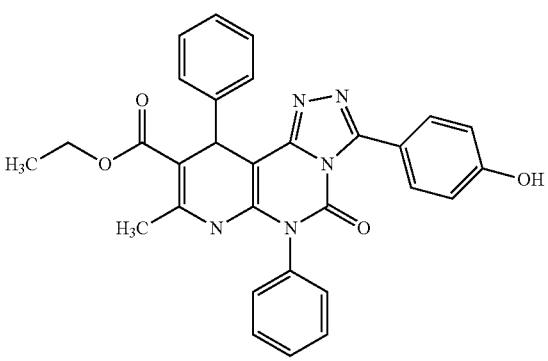
13
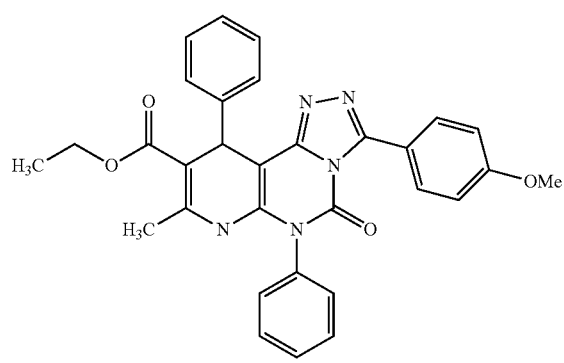
17

18
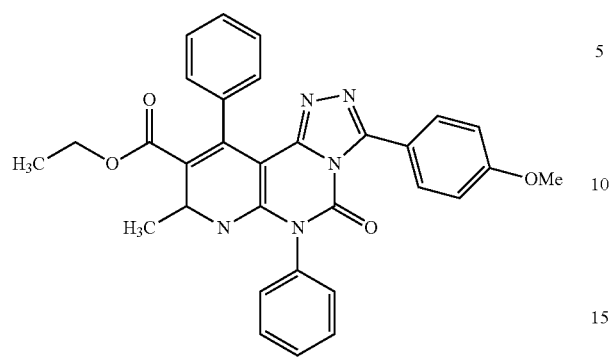
19
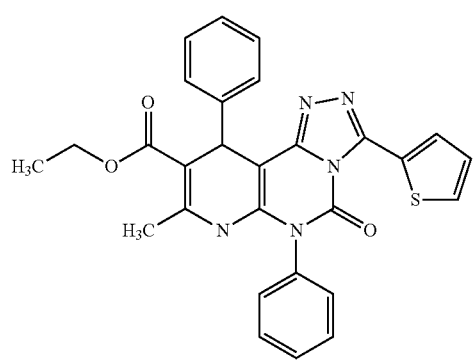
20
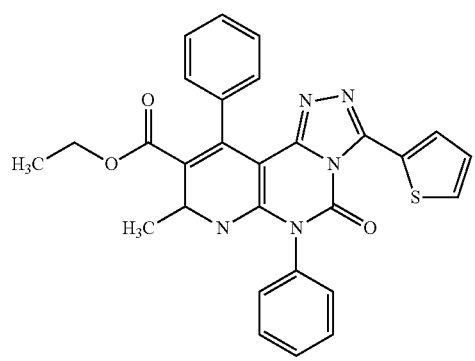
21
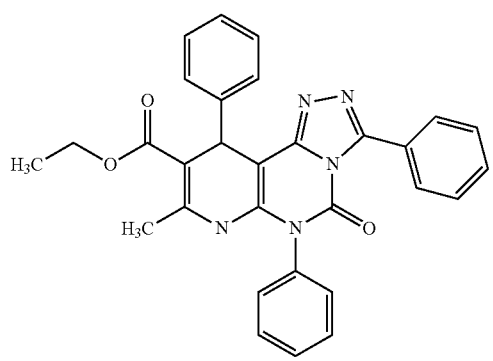
22
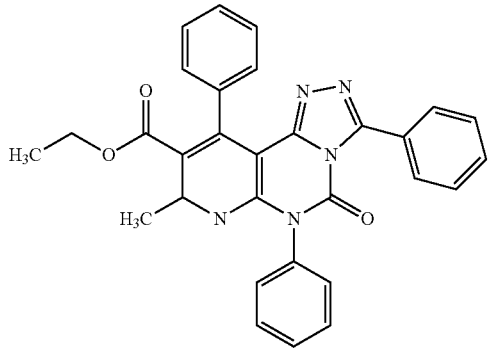
23
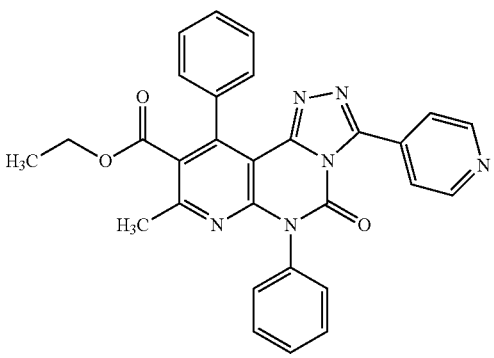
24
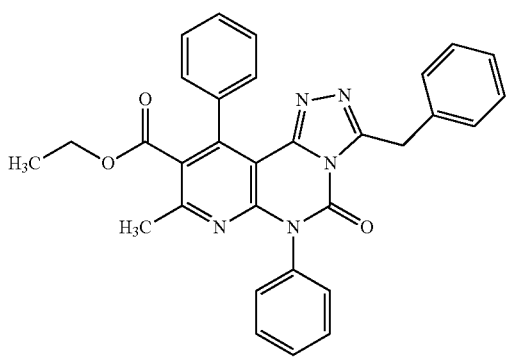
25
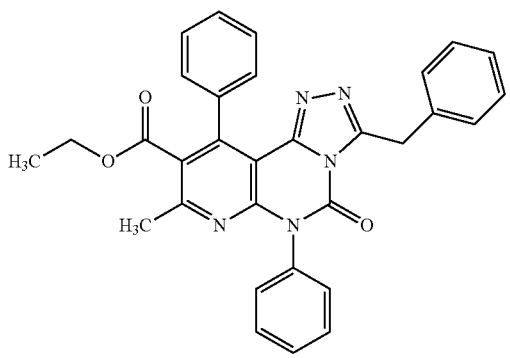

26
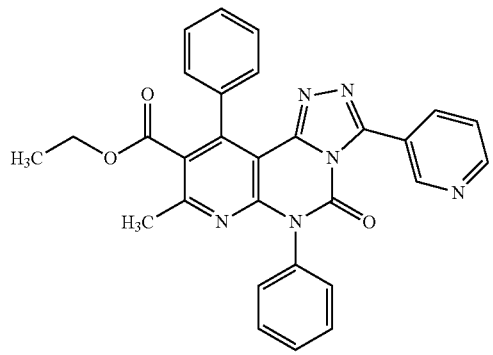
27
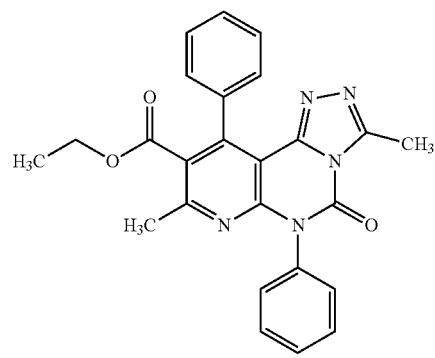
28
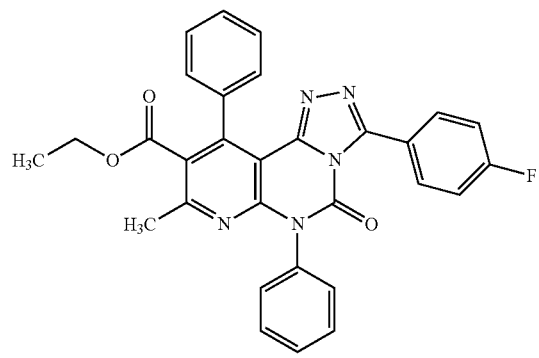
29
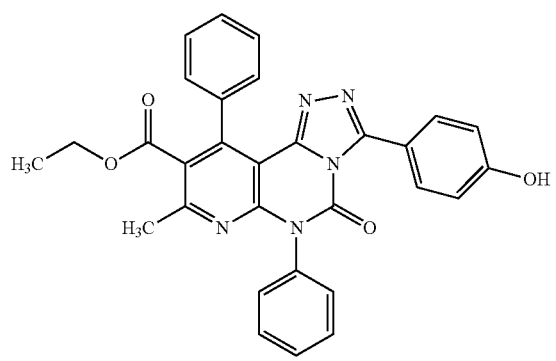
30
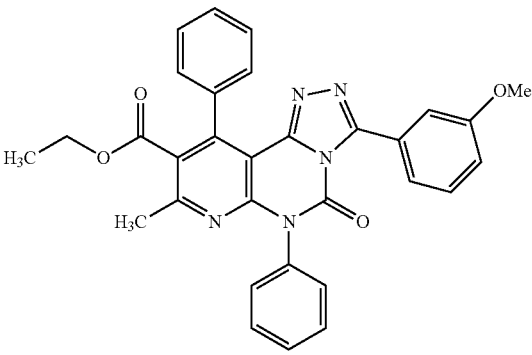 [SMILES: CCOC(=O)c1c(C)nc2c(c1-c1ccccc1)c1nnc(-c3cccc(OC)c3)n1c(=O)n2-c1ccccc1]
31
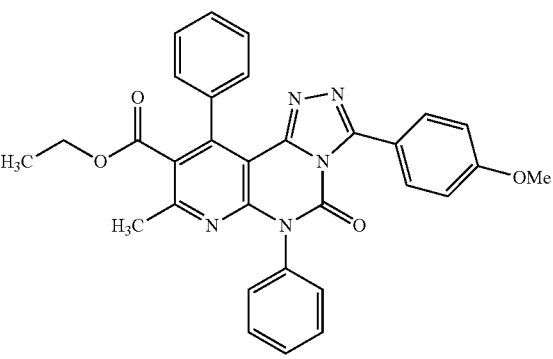 [SMILES: CCOC(=O)c1c(C)nc2c(c1-c1ccccc1)c1nnc(-c3ccc(OC)cc3)n1c(=O)n2-c1ccccc1]
32
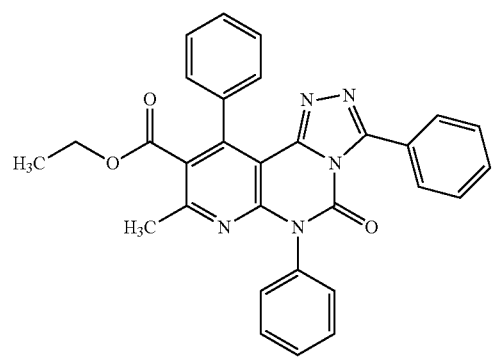 [SMILES: CCOC(=O)c1c(C)nc2c(c1-c1ccccc1)c1nnc(-c3ccccc3)n1c(=O)n2-c1ccccc1]
33

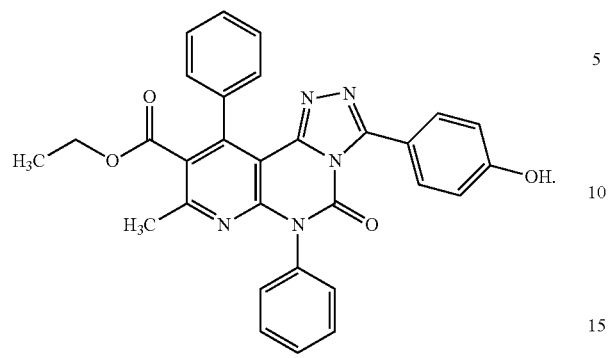
34
* * * * *